(12) United States Patent
Tamir et al.

(10) Patent No.: US 12,667,690 B2
(45) Date of Patent: Jun. 30, 2026

(54) EXPANDABLE SHEATH FOR INTRODUCING AN ENDOVASCULAR DELIVERY DEVICE INTO A BODY

(71) Applicant: EDWARDS LIFESCIENCES CORPORATION, Irvine, CA (US)

(72) Inventors: Ilan Tamir, Irvine, CA (US); Devin H. Marr, Westford, MA (US); David A. Rezac, Lancaster, MA (US); Michelle Riches, Leominster, MA (US); Bridget Bergstrom, Maple Grove, MN (US); Julia Stoddard, Harvard, MA (US)

(73) Assignee: Edwards Lifesciences Corporation, Irvine, CA (US)

( * ) Notice: Subject to any disclaimer, the term of this patent is extended or adjusted under 35 U.S.C. 154(b) by 492 days.

(21) Appl. No.: 18/137,830

(22) Filed: Apr. 21, 2023

(65) Prior Publication Data

US 2023/0256195 A1     Aug. 17, 2023

Related U.S. Application Data

(63) Continuation of application No. PCT/US2021/056158, filed on Oct. 22, 2021.

(60) Provisional application No. 63/105,130, filed on Oct. 23, 2020.

(51) Int. Cl.
      A61M 25/00          (2006.01)
      A61M 25/01          (2006.01)
(52) U.S. Cl.
      CPC ........ A61M 25/0023 (2013.01); A61M 25/01 (2013.01); A61M 2025/0024 (2013.01)

(58) Field of Classification Search
      CPC .............. A61M 25/0023; A61M 25/01; A61M 2025/0024; A61M 25/0045;
      (Continued)

(56)                   References Cited

U.S. PATENT DOCUMENTS

| | | |
|---|---|---|
| 4,601,713 A | 7/1986 | Fuqua |
| 4,710,181 A | 12/1987 | Fuqua |

(Continued)

FOREIGN PATENT DOCUMENTS

| | | |
|---|---|---|
| EP | 0103546 B1 | 5/1988 |
| EP | 0592410 B1 | 10/1995 |

(Continued)

*Primary Examiner* — Jason E Flick
(74) *Attorney, Agent, or Firm* — Meunier Carlin Curfman LLC

(57)                   ABSTRACT

Aspects of an expandable sheath can be used in conjunction with a catheter assembly to introduce a prosthetic device, such as a heart valve, into a patient. Such aspects can minimize trauma to the vessel by allowing for temporary expansion of a portion of the introducer sheath to accommodate the delivery apparatus, followed by a return to the original diameter once the prosthetic device passes through. Some aspects can include a sheath comprising an inner layer comprising a reinforcing layer rolled into a spiral slidable configuration and encapsulated within a polymer layer comprising a tether portion and an outer layer disposed over the inner layer. The disclosed sheath is configured to locally expand from a predetermined first diameter $d_1$ to an expanded second diameter $d_2$ during application of a radial outward force by passage of the medical device through the sheath.

20 Claims, 19 Drawing Sheets

(58) Field of Classification Search
CPC ...... A61M 2025/0681; A61M 25/0051; A61M
25/0662; A61M 2025/0047; A61M
25/0012; A61F 2/2436; A61F 2/24; A61F
2/958; A61F 2/962
See application file for complete search history.

(56) References Cited

U.S. PATENT DOCUMENTS

| | | | |
|---|---|---|---|
| 4,738,666 | A | 4/1988 | Fuqua |
| 4,921,479 | A | 5/1990 | Grayzel |
| 5,104,388 | A | 4/1992 | Quackenbush |
| 5,318,588 | A | 6/1994 | Horzewski et al. |
| 5,320,611 | A | 6/1994 | Bonutti et al. |
| 5,501,667 | A | 3/1996 | Verduin |
| 5,674,240 | A | 10/1997 | Bonutti et al. |
| 5,810,776 | A | 9/1998 | Bacich et al. |
| 5,817,100 | A | 10/1998 | Igaki |
| 5,882,345 | A | 3/1999 | Yoon |
| 5,997,508 | A | 12/1999 | Lunn et al. |
| 6,080,141 | A | 6/2000 | Castro et al. |
| 6,090,072 | A | 7/2000 | Kratoska et al. |
| 6,090,136 | A | 7/2000 | McDonald et al. |
| 6,190,357 | B1 | 2/2001 | Ferrari et al. |
| 6,312,443 | B1 | 11/2001 | Stone |
| 6,346,092 | B1 | 2/2002 | Leschinsky |
| 6,358,238 | B1 | 3/2002 | Sherry |
| 6,443,979 | B1 | 9/2002 | Stalker et al. |
| 6,494,860 | B2 | 12/2002 | Rocamora et al. |
| 6,632,236 | B2 | 10/2003 | Hogendijk |
| 6,652,492 | B1 | 11/2003 | Bell et al. |
| 6,814,715 | B2 | 11/2004 | Bonutti et al. |
| 6,899,727 | B2 | 5/2005 | Armstrong et al. |
| 7,438,712 | B2 | 10/2008 | Chouinard |
| 7,591,832 | B2 | 9/2009 | Eversull et al. |
| 7,655,016 | B2 | 2/2010 | Demarais et al. |
| 7,678,128 | B2 | 3/2010 | Boyle et al. |
| 7,713,193 | B2 | 5/2010 | Nance et al. |
| 7,762,995 | B2 | 7/2010 | Eversull et al. |
| 7,766,820 | B2 | 8/2010 | Core |
| 7,780,692 | B2 | 8/2010 | Nance et al. |
| 7,785,360 | B2 | 8/2010 | Freitag |
| 7,837,692 | B2 | 11/2010 | Mulholland et al. |
| 7,892,203 | B2 | 2/2011 | Lenker et al. |
| 7,927,309 | B2 | 4/2011 | Palm |
| 7,963,952 | B2 | 6/2011 | Wright et al. |
| 8,034,072 | B2 | 10/2011 | Nguyen et al. |
| 8,048,034 | B2 | 11/2011 | Eversull et al. |
| 8,090,936 | B2 | 1/2012 | Fallon et al. |
| 8,092,481 | B2 | 1/2012 | Nance et al. |
| 8,252,015 | B2 | 8/2012 | Leeflang et al. |
| 8,282,664 | B2 | 10/2012 | Nance et al. |
| 8,414,645 | B2 | 4/2013 | Dwork et al. |
| 8,562,559 | B2 | 10/2013 | Bishop et al. |
| 8,562,673 | B2 | 10/2013 | Yeung et al. |
| 8,652,203 | B2 | 2/2014 | Quadri et al. |
| 8,668,668 | B2 | 3/2014 | Bishop et al. |
| 8,690,936 | B2 | 4/2014 | Nguyen et al. |
| 8,790,387 | B2 | 7/2014 | Nguyen et al. |
| 9,044,577 | B2 | 6/2015 | Bishop et al. |
| 9,192,751 | B2 | 11/2015 | Macaulay et al. |
| 9,192,752 | B2 | 11/2015 | Leeflang et al. |
| 9,254,374 | B2 | 2/2016 | Thorstenson et al. |
| 9,259,813 | B2 | 2/2016 | Heideman et al. |
| 9,301,840 | B2 | 4/2016 | Nguyen et al. |
| 9,301,841 | B2 | 4/2016 | Nguyen et al. |
| 9,320,508 | B2 | 4/2016 | Carroux |
| 9,393,041 | B2 | 7/2016 | Barker et al. |
| 9,642,704 | B2 | 5/2017 | Tuval et al. |
| 9,788,944 | B2 | 10/2017 | Daly et al. |
| 9,907,931 | B2 | 3/2018 | Birmingham et al. |
| 10,327,896 | B2 | 6/2019 | Zhou et al. |
| 10,639,152 | B2 | 5/2020 | Le et al. |
| 10,792,471 | B2 | 10/2020 | Zhou et al. |
| 10,912,919 | B2 | 2/2021 | Bulman et al. |
| 11,344,698 | B2 | 5/2022 | Worthley et al. |

| | | | | |
|---|---|---|---|---|
| 2001/0012950 | A1 | 8/2001 | Nishtala et al. | |
| 2002/0032459 | A1 | 3/2002 | Horzewski et al. | |
| 2002/0099431 | A1 | 7/2002 | Armstrong et al. | |
| 2002/0123793 | A1 | 9/2002 | Schaldach et al. | |
| 2002/0128702 | A1 | 9/2002 | Menz et al. | |
| 2003/0004537 | A1 | 1/2003 | Boyle et al. | |
| 2004/0087968 | A1 | 5/2004 | Core | |
| 2004/0122415 | A1 | 6/2004 | Johnson | |
| 2005/0080430 | A1 | 4/2005 | Wright et al. | |
| 2005/0085842 | A1 | 4/2005 | Eversull et al. | |
| 2005/0125021 | A1 | 6/2005 | Nance et al. | |
| 2006/0020321 | A1 | 1/2006 | Parker | |
| 2006/0135962 | A1 | 6/2006 | Kick et al. | |
| 2006/0135981 | A1 | 6/2006 | Lenker et al. | |
| 2006/0217755 | A1 | 9/2006 | Eversull et al. | |
| 2007/0021768 | A1 | 1/2007 | Nance et al. | |
| 2007/0074805 | A1 | 4/2007 | Leeflang et al. | |
| 2007/0087148 | A1 | 4/2007 | Okushi et al. | |
| 2008/0004521 | A1 | 1/2008 | Hundley et al. | |
| 2008/0004571 | A1 | 1/2008 | Voss | |
| 2008/0114331 | A1 | 5/2008 | Holman et al. | |
| 2008/0243081 | A1 | 10/2008 | Nance et al. | |
| 2009/0182411 | A1 | 7/2009 | Irwin et al. | |
| 2009/0287182 | A1 | 11/2009 | Bishop et al. | |
| 2010/0094209 | A1 | 4/2010 | Drasler et al. | |
| 2010/0094392 | A1 | 4/2010 | Nguyen et al. | |
| 2010/0198160 | A1 | 8/2010 | Voss | |
| 2010/0324490 | A1 | 12/2010 | Pini et al. | |
| 2011/0112567 | A1 | 5/2011 | Lenker et al. | |
| 2011/0190697 | A1 | 8/2011 | Farnan | |
| 2011/0251681 | A1 | 10/2011 | Shipley et al. | |
| 2012/0083877 | A1* | 4/2012 | Nguyen | A61F 2/2418 623/2.11 |
| 2012/0116439 | A1 | 5/2012 | Ho | |
| 2012/0158033 | A1 | 6/2012 | Deal et al. | |
| 2012/0323180 | A1 | 12/2012 | Chebator et al. | |
| 2013/0090624 | A1 | 4/2013 | Munsinger | |
| 2013/0131718 | A1 | 5/2013 | Jenson et al. | |
| 2013/0178711 | A1 | 7/2013 | Avneri et al. | |
| 2013/0211324 | A1 | 8/2013 | Voss et al. | |
| 2013/0231735 | A1 | 9/2013 | Deem et al. | |
| 2013/0268064 | A1 | 10/2013 | Duffy | |
| 2013/0281787 | A1 | 10/2013 | Avneri et al. | |
| 2014/0012281 | A1 | 1/2014 | Wang et al. | |
| 2014/0121629 | A1 | 5/2014 | Macaulay et al. | |
| 2014/0142509 | A1 | 5/2014 | Bonutti et al. | |
| 2014/0236122 | A1 | 8/2014 | Anderson et al. | |
| 2014/0236123 | A1 | 8/2014 | Birmingham et al. | |
| 2014/0379067 | A1 | 12/2014 | Nguyen et al. | |
| 2015/0112428 | A1 | 4/2015 | Daly et al. | |
| 2015/0182723 | A1 | 7/2015 | Leeflang et al. | |
| 2015/0238178 | A1 | 8/2015 | Carroux | |
| 2015/0265798 | A1 | 9/2015 | Nihonmatsu et al. | |
| 2015/0320971 | A1 | 11/2015 | Leeflang et al. | |
| 2016/0074067 | A1 | 3/2016 | Furnish et al. | |
| 2016/0135840 | A1 | 5/2016 | Kick et al. | |
| 2016/0213882 | A1 | 7/2016 | Fitterer et al. | |
| 2016/0296332 | A1 | 10/2016 | Zhou et al. | |
| 2016/0296730 | A1 | 10/2016 | Zhou et al. | |
| 2017/0014157 | A1* | 1/2017 | Coyle | A61M 25/0023 |
| 2017/0072163 | A1 | 3/2017 | Lim et al. | |
| 2017/0196690 | A1 | 7/2017 | Racchini et al. | |
| 2017/0209133 | A1 | 7/2017 | Ciulla et al. | |
| 2017/0245864 | A1 | 8/2017 | Franano et al. | |
| 2017/0252062 | A1 | 9/2017 | Fitterer et al. | |
| 2018/0043133 | A1 | 2/2018 | Wong | |
| 2018/0161064 | A1 | 6/2018 | Fitterer et al. | |
| 2018/0199960 | A1 | 7/2018 | Anderson et al. | |
| 2018/0207395 | A1 | 7/2018 | Bulman et al. | |
| 2018/0229000 | A1 | 8/2018 | Anderson et al. | |
| 2018/0256858 | A1* | 9/2018 | Zhou | A61F 2/2436 |
| 2018/0325549 | A1 | 11/2018 | Thoreson et al. | |
| 2019/0076167 | A1 | 3/2019 | Fantuzzi et al. | |
| 2019/0083082 | A1 | 3/2019 | Tassoni, Jr. et al. | |
| 2019/0192290 | A1 | 6/2019 | Pfenniger et al. | |
| 2019/0247627 | A1 | 8/2019 | Korkuch et al. | |
| 2019/0269510 | A1 | 9/2019 | Zeng et al. | |
| 2020/0078571 | A1 | 3/2020 | Kirt et al. | |
| 2021/0008344 | A1 | 1/2021 | Chen et al. | |

(56) References Cited

U.S. PATENT DOCUMENTS

| | | |
|---|---|---|
| 2021/0236783 A1 | 8/2021 | Korkuch et al. |
| 2022/0032015 A1 | 2/2022 | Campbell et al. |
| 2022/0346950 A1 | 11/2022 | Le et al. |
| 2023/0029387 A1 | 1/2023 | Yadav et al. |
| 2023/0069245 A1 | 3/2023 | Tran et al. |
| 2023/0149674 A1 | 5/2023 | Neumann et al. |
| 2023/0381455 A1 | 11/2023 | Fantuzzi et al. |
| 2024/0091038 A1 | 3/2024 | Acharya |
| 2024/0299722 A1 | 9/2024 | Ruiz et al. |
| 2025/0001139 A1 | 1/2025 | Farrell et al. |
| 2025/0144367 A1 | 5/2025 | Anderson et al. |
| 2025/0249213 A1 | 8/2025 | Belcher et al. |
| 2025/0276153 A1 | 9/2025 | Moran et al. |
| 2025/0276155 A1 | 9/2025 | Moran et al. |
| 2025/0367411 A1 | 12/2025 | Mak et al. |

FOREIGN PATENT DOCUMENTS

| | | | |
|---|---|---|---|
| EP | 1139889 | B1 | 4/2006 |
| EP | 1793881 | A2 | 6/2007 |
| EP | 1804860 | B1 | 4/2014 |
| EP | 2288403 | B1 | 11/2014 |
| EP | 1694398 | B1 | 3/2016 |
| EP | 2101661 | B1 | 3/2016 |
| EP | 2995268 | A1 | 3/2016 |
| EP | 2475417 | B1 | 10/2018 |
| EP | 2911729 | B1 | 12/2018 |
| EP | 2862590 | B1 | 2/2019 |
| EP | 1793881 | B1 | 4/2020 |
| JP | 2012040145 | A | 3/2012 |
| WO | 2004037333 | A1 | 5/2004 |
| WO | 2008147964 | A1 | 12/2008 |
| WO | 2009035745 | A1 | 3/2009 |
| WO | 2013044942 | A1 | 4/2013 |
| WO | 2014140093 | A1 | 9/2014 |
| WO | WO-2015063497 | A1 | 5/2015 |
| WO | 2018148488 | A1 | 8/2018 |
| WO | 2022026026 | A1 | 2/2022 |
| WO | WO-2024205785 | A1 | 10/2024 |
| WO | WO-2024226928 | A1 | 10/2024 |
| WO | WO-2024263844 | A1 | 12/2024 |
| WO | WO-2025029777 | A1 | 2/2025 |
| WO | WO-2025048911 | A1 | 3/2025 |

* cited by examiner

EXPANDABLE SHEATH FOR INTRODUCING AN ENDOVASCULAR DELIVERY DEVICE INTO A BODY

CROSS-REFERENCE TO RELATED APPLICATIONS

This application is a continuation of International Application No. PCT/US2021/056158, filed Oct. 22, 2021, which claims the benefit of U.S. Provisional Application No. 63/105,130, filed Oct. 23, 2020, the contents of which are incorporated herein by reference in their entirety.

FIELD

The present application refers to a sheath for use with catheter-based technologies for repairing and/or replacing heart valves and delivering a prosthetic device, such as a prosthetic valve to a heart via the patient's vasculature.

BACKGROUND

Endovascular delivery catheter assemblies are used to implant prosthetic devices, such as a prosthetic valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for a valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes and the risk of damage to the vessel.

Radially expanding intravascular sheaths have been disclosed. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a significant risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque.

Accordingly, there remains a need in the art for an improved introducer sheath for endovascular systems used for implanting valves and other prosthetic devices.

SUMMARY

As disclosed herein, the expandable sheath can minimize trauma to the vessel by allowing for temporary expansion of a portion of the introducer sheath to accommodate a delivery system, followed by a return to the original diameter once the delivery system passes through. In some aspects, disclosed herein is a sheath with a smaller profile than that of prior art introducer sheaths. Furthermore, in certain aspects, the sheath of the present disclosure can reduce the length of time a procedure takes, as well as reduce the risk of a longitudinal or radial vessel tear or plaque dislodgement because only one sheath is required rather than several different sizes of sheaths. In certain aspects, the present expandable sheath can require only a single vessel insertion, as opposed to requiring multiple insertions for the dilation of the vessel.

In one aspect, disclosed herein is a sheath for introducing a prosthetic device comprising an inner layer and an outer layer. In such aspects, at least a portion of the sheath can be designed or configured to locally expand from a first diameter (rest diameter) to a second diameter (expanded diameter) as the prosthetic device is pushed through a lumen of the sheath and then at least partially return to the first diameter once the prosthetic device has passed through.

Also disclosed herein one aspect of a sheath for delivering a medical device, wherein the sheath has a proximal and a distal end and comprises: a) an inner layer comprising: i) a reinforcing layer having an inner surface and an outer surface and a first longitudinal edge and an opposite second longitudinal edge, and wherein the reinforcing layer has a width extending from the first edge to the second edge; ii) a polymer layer; and b) an outer layer; wherein the reinforcing layer is rolled longitudinally into a spiral configuration such that at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration; wherein the polymer layer extends circumferentially around the reinforcing layer such that the reinforcing layer is substantially encapsulated within the polymer layer; wherein the polymer layer comprises a tether portion that is substantially free of the reinforcing layer; wherein the polymer layer forms a substantially circular enclosed shape of the inner layer; wherein the inner layer forms a lumen configured to receive the medical device; wherein the sheath is in an unexpanded state, the lumen has a first diameter; and wherein the lumen is configured to expand to a second diameter by sliding the first edge of the reinforcing layer along at least a portion of the inner surface of the reinforcing layer and sliding the second edge of the reinforcing layer along the at least a portion of the outer surface of the reinforcing layer, during application of a radial outward force by passage of the medical device through the lumen.

In certain aspects, when the sheath is in the unexpanded state, the overlapping portion comprises about 30-70% of the reinforcing layer width. While in other aspects, when the sheath is in the expanded state, the overlapping portion comprises about 10-20% of the reinforcing layer width.

Still, in further aspects, in addition, or in alternative to the sheath disclosed in any previous aspects, the sheath is substantially kink-resistant.

Also disclosed herein are aspects comprising methods of making a sheath for delivering a medical device. In certain aspects, the method of making such a sheath comprises rolling a reinforcing layer having an inner surface and an outer surface and a first longitudinal edge and an opposite second longitudinal edge and a width extending from the first edge to the second edge into a spiral configuration around a first mandrel having a first diameter to form a lumen having a rest diameter substantially identical to the first diameter of the mandrel, such that in the spiral configuration, at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration; removing the first mandrel; inserting a second mandrel having a second diameter larger than the first diameter into the lumen and thereby expanding the lumen to the second diameter by sliding the first edge of the reinforcing layer along at least a portion of the inner surface of the reinforcing layer and sliding the second edge of the reinforcing layer along the at least a portion of the outer surface of the reinforcing layer until the overlapping portion is substantially eliminated and a slit is formed between the first edge and the second edge of the reinforcing layer; applying a polymer layer radially outward of the reinforcing layer under conditions effective to encapsulate the reinforcing layer with the polymer layer such that the polymer layer forms a tether portion that is substantially free of the reinforcing layer and wherein the reinforcing layer and the polymer layer together form an inner layer of the sheath; and removing the inner layer from the second mandrel to allow the reinforcing layer to return to the spiral configuration having a lumen having a diameter substantially identical to the rest diameter; and positioning the inner layer on the first mandrel and applying an outer layer radially outward of the inner layer of the sheath and removing the sheath from the first mandrel.

In still further exemplary aspects, the conditions effective to encapsulate the reinforcing layer with the polymer layer can comprise a sintering step.

In still further aspects, the overlapping portion of the spiral configuration having the lumen having the rest diameter comprises about 30-70% of the reinforcing layer width.

In certain aspects of the methods disclosed herein, the lumen can be configured to expand to an expanded diameter upon passage of the medical device through the lumen by decreasing the overlapping portion of the spiral configuration. In such exemplary and unlimiting aspects, the overlapping portion comprises about 10-20% of the reinforcing layer width.

Also in some aspects disclosed herein is a method of delivering a medical device through a sheath, the method comprising: a) introducing the medical device into a proximal end of a lumen having a first diameter and wherein the lumen is formed by an inner layer, wherein the inner layer comprises: i) a reinforcing layer having an inner surface and an outer surface and a first longitudinal edge and an opposite second longitudinal edge, and wherein the reinforcing layer has a width extending from the first edge to the second edge; and ii) a polymer layer; wherein the reinforcing layer is rolled longitudinally into a spiral configuration such that at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration, wherein the polymer layer extends circumferentially around the reinforcing layer such that the reinforcing layer is substantially encapsulated within the polymer layer; wherein the polymer layer comprises a tether portion that is substantially free of the reinforcing layer; and wherein the polymer layer forms a substantially circular enclosed shape of the inner layer; b) advancing the medical device through the lumen such that the medical device exerts a radially outward force on the inner layer, such that the lumen expands to a second diameter by sliding the first edge of the reinforcing layer along at least a portion of the inner surface of the reinforcing layer and sliding the second edge of the reinforcing layer along the at least a portion of the outer surface of the reinforcing layer; and c) locally contracting the expanded sheath back to an unexpanded configuration by radially compressing the expanded portion with a radially inward bias of an outer layer that extends around the inner layer.

In still further aspects of the methods disclosed herein, the medical device is a prosthetic heart valve mounted in a radially crimped state on a delivery apparatus, and the act of advancing the medical device through the sheath comprises advancing the delivery apparatus and the prosthetic heart valve into the vasculature of a patient.

In some methods, a soft tip portion can be coupled to the distal end of the expandable sheath to facilitate passing the expandable sheath through a patient's vasculature.

The foregoing and other features and advantages of the invention will become more apparent from the following detailed description, which proceeds with reference to the accompanying figures.

BRIEF DESCRIPTION OF DRAWINGS

FIG. 3A shows a perspective schematic of an expanded sheath in another aspect. FIG. 3B shows a cross-section view of the expanded sheath depicted in FIG. 3A.

DETAILED DESCRIPTION

Figure 1:
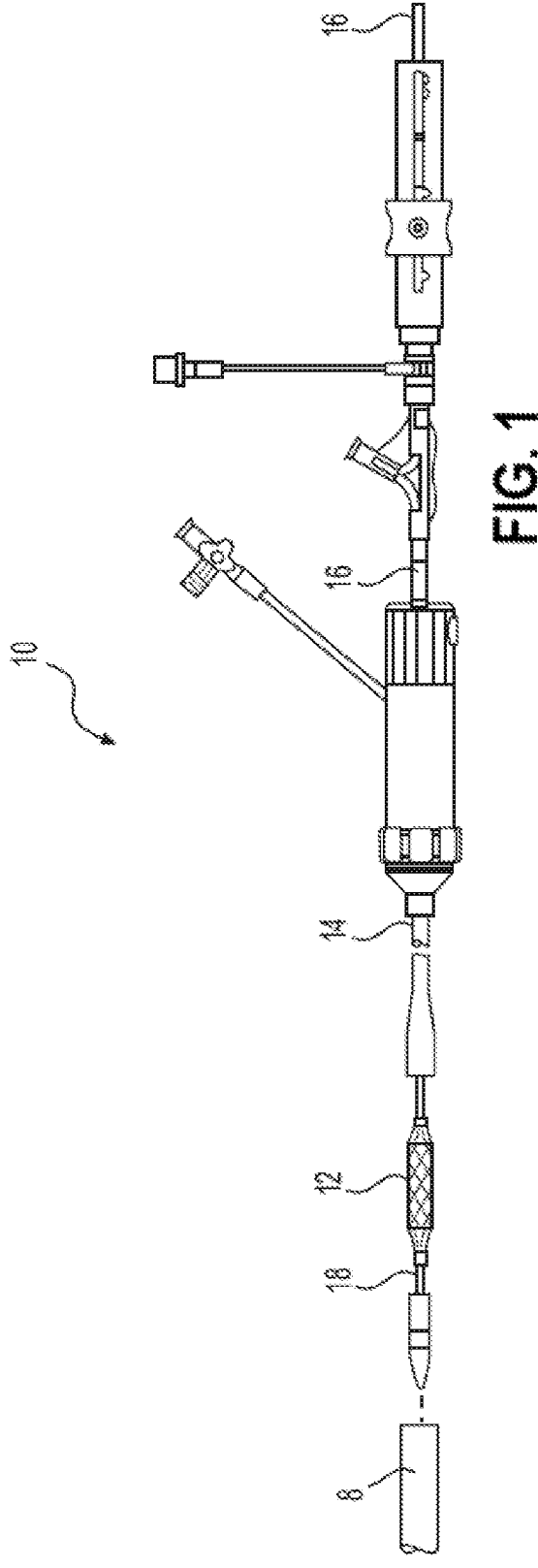
FIG. 1 is an elevation view of a sheath according to the present disclosure along with an endovascular delivery apparatus for implanting a prosthetic valve.

The present invention can be understood more readily by reference to the following detailed description, examples, drawings, and claims, and their previous and following description. However, before the present articles, systems, and/or methods are disclosed and described, it is to be understood that this invention is not limited to the specific or exemplary aspects of articles, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. To this end, those skilled in the relevant art will recognize and appreciate that many changes can be made to the various aspects of the invention described herein while still obtaining the beneficial results of the present invention. It will also be apparent that some of the desired benefits of the present invention can be obtained by selecting some of the features of the present invention without utilizing other features. Accordingly, those of ordinary skill in the pertinent art will recognize that many modifications and adaptations to the present invention are possible and may even be desirable in certain circumstances and are a part of the present invention. Thus, the following description is again provided as illustrative of the principles of the present invention and not in limitation thereof.

Definitions

Unless defined otherwise, all technical and scientific terms used herein have the same meaning as commonly understood by one of ordinary skill in the art to which this invention belongs.

As used in this application and in the claims, the singular forms "a," "an," and "the" include the plural forms unless the context clearly dictates otherwise. Thus, for example, reference to a "polymer" includes aspects having two or more such polymers unless the context clearly indicates otherwise.

It is also to be understood that the terminology used herein is for the purpose of describing particular aspects only and is not intended to be limiting. As used in the specification and in the claims, the term "comprising" can include the aspects "consisting of" and "consisting essentially of." Additionally, the term "includes" means "comprises."

For the terms "for example" and "such as," and grammatical equivalences thereof, the phrase "and without limitation" is understood to follow unless explicitly stated otherwise.

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

A weight percent of a component, unless specifically stated to the contrary, is based on the total weight of the formulation or composition in which the component is included.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value and/or to "about" another particular value. When such a range is expressed, another aspect includes from the one particular value and/or to the other particular value.

Similarly, when values are expressed as approximations, by use of the antecedent "about," it will be understood that the particular value forms another aspect. It will be further understood that the endpoints of each of the ranges are significant both in relation to the other endpoint and independently of the other endpoint. Unless stated otherwise, the term "about" means within 5% (e.g., within 2% or 1%) of the particular value modified by the term "about."

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6 and any whole and partial increments therebetween. This applies regardless of the breadth of the range.

As used herein, the term "substantially," when used in reference to a composition, refers to at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature or component.

As used herein, the term "substantially," when used in the context of a composition or component of a composition that is substantially absent, is intended to indicate that the recited component is not intentionally batched and added to the composition but can be present as an impurity along with other components being added to the composition. In such aspects, the term "substantially free," is intended to refer to trace amounts that can be present in the batched components, for example, it can be present in an amount that is less than about 1% by weight, e.g., less than about 0.5% by weight, less than about 0.1% by weight, less than about 0.05% by weight, or less than about 0.01% by weight of the stated material, based on the total weight of the composition.

As used herein, the terms "substantially identical reference composition" or "substantially identical reference article" refer to a reference composition or article comprising substantially identical components in the absence of an inventive component. In another exemplary aspect, the term "substantially," in, for example, the context "substantially identical reference composition," refers to a reference composition comprising substantially identical components and wherein an inventive component is substituted with a common in the art component.

As used herein, the terms "substantially near" or "substantially abut" refer to a disclosed component, element, member, or article being positioned within at least about 85%, at least about 90%, at least about 91%, at least about 92%, at least about 93%, at least about 94%, at least about 95%, at least about 96%, at least about 97%, at least about 98%, at least about 99%, or about 100% of a component, element, member or article that it is described in reference to.

Further, the terms "coupled" and "associated" generally mean electrically, electromagnetically, and/or physically (e.g., mechanically or chemically) coupled or linked and do not exclude the presence of intermediate elements between the coupled or associated items.

It will be understood that when an element is referred to as being "connected" or "coupled" to another element, it can be directly connected or coupled to the other element, or intervening elements may be present. In contrast, when an element is referred to as being "directly connected" or "directly coupled" to another element, there are no intervening elements present. Other words used to describe the relationship between elements or layers should be interpreted in a like fashion (e.g., "between" versus "directly between," "adjacent" versus "directly adjacent," "on" versus "directly on").

As used herein, the term "and/or" includes any and all combinations of one or more of the associated listed items.

It will be understood that, although the terms "first," "second," etc., may be used herein to describe various elements, components, regions, layers, and/or sections. These elements, components, regions, layers, and/or sections should not be limited by these terms. These terms are only used to distinguish one element, component, region, layer, or section from another element, component, region, layer, or a section. Thus, a first element, component, region, layer, or section discussed below could be termed a second element, component, region, layer, or section without departing from the teachings of exemplary aspects.

Spatially relative terms, such as "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 90 degrees or at other orientations), and the spatially relative descriptors used herein interpreted accordingly.

As used herein, the term "atraumatic" is commonly known in the art and refers to a device or a procedure that minimized tissue injury.

As used herein, the term or phrase "effective," "effective amount," or "conditions effective to" refers to such amount or condition that is capable of performing the function or property for which an effective amount or condition is expressed. As will be pointed out below, the exact amount or particular condition required will vary from one aspect to another, depending on recognized variables such as the materials employed and the processing conditions observed. Thus, it is not always possible to specify an exact "effective amount" or "condition effective to." However, it should be understood that an appropriate effective amount will be readily determined by one of ordinary skill in the art using only routine experimentation.

While aspects of the present invention can be described and claimed in a particular statutory class, such as the system statutory class, this is for convenience only, and one of ordinary skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred in any respect. This holds for any possible non-express basis for interpretation, including matters of logic with respect to arrangement of steps or operational flow, plain meaning derived from grammatical organization or punctuation, or the number or type of aspects described in the specification.

Although the operations of exemplary aspects of the disclosed method may be described in a particular sequential order for convenient presentation, it should be understood that disclosed aspects can encompass an order of operations other than the particular sequential order disclosed. For example, operations described sequentially may, in some cases, be rearranged or performed concurrently. Further, descriptions and disclosures provided in association with one particular aspect are not limited to that aspect and may be applied to any aspect disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Sheath

Disclosed aspects of an expandable sheath can minimize trauma to the vessel by allowing for temporary expansion of a portion of the introducer sheath to accommodate the delivery system, followed by a return to the original diameter once the device passes through. Some aspects can comprise a sheath with a smaller profile (e.g., a smaller diameter in the rest configuration) than that of prior art introducer sheaths. Furthermore, present aspects can reduce the length of time a procedure takes, as well as reduce the risk of a longitudinal or radial vessel tear or plaque dislodgement because only one sheath is required, rather than several different sizes of sheaths. In some disclosed aspects, the expandable sheath, as described herein, can avoid the need for multiple insertions for the dilation of the vessel. Such expandable sheaths can be useful for many types of minimally invasive surgery, such as any surgery requiring introduction of an apparatus into a subject's vessel. For example, the sheath can be used to introduce other types of delivery apparatus for placing various types of intraluminal devices (e.g., stents, prosthetic heart valves, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

FIG. 1 illustrates a sheath 8 according to the present disclosure, in use with a representative delivery apparatus 10, for delivering a prosthetic device 12, such as a tissue heart valve to a patient. The apparatus 10 can include a steerable guide catheter 14 (also referred to as a flex catheter), a balloon catheter 16 extending through the guide catheter 14, and a nose catheter 18 extending through the balloon catheter 16. The guide catheter 14, the balloon catheter 16, and the nose catheter 18 in the illustrated aspect are adapted to slide longitudinally relative to each other to facilitate delivery and positioning of the valve 12 at an implantation site in a patient's body, as described in detail below. Generally, sheath 8 is inserted into a vessel, such as the transfemoral vessel, passing through the skin of the patient, such that the distal end of the sheath 8 is inserted into the vessel. Sheath 8 can include a hemostasis valve at the opposite, proximal end of the sheath. The delivery apparatus 10 can be inserted into the sheath 8, and the prosthetic device 12 can then be delivered and implanted within the patient.

Figure 2A:
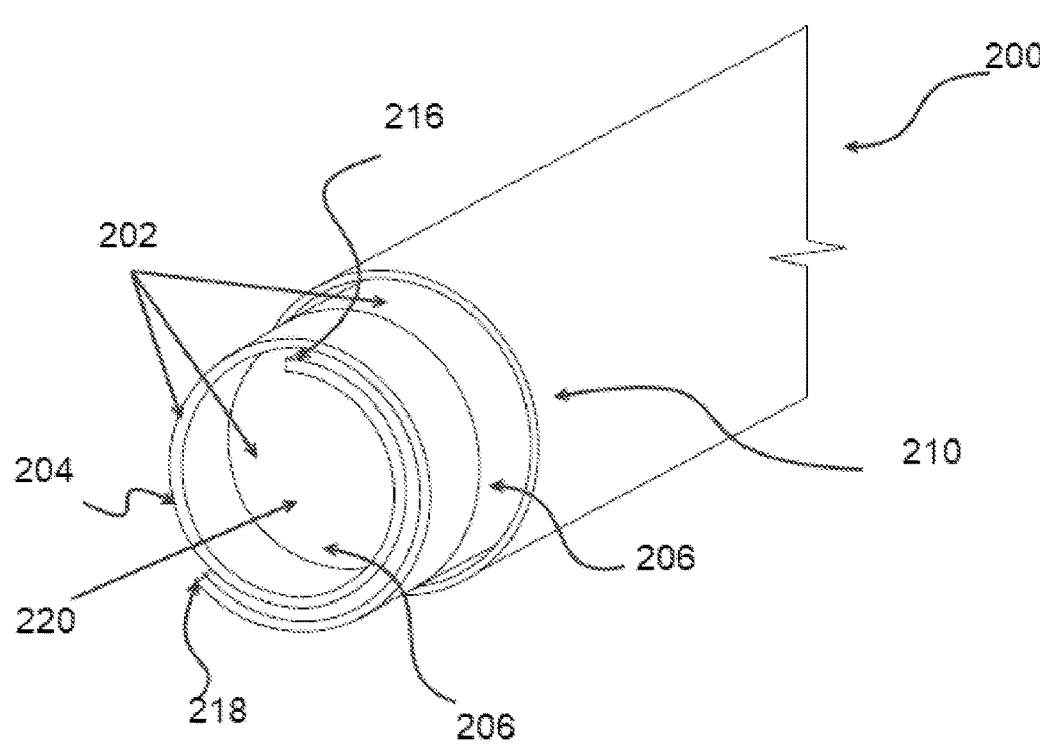
FIG. 2A depicts a perspective schematic of an unexpanded sheath in one aspect.
Figure 2B:
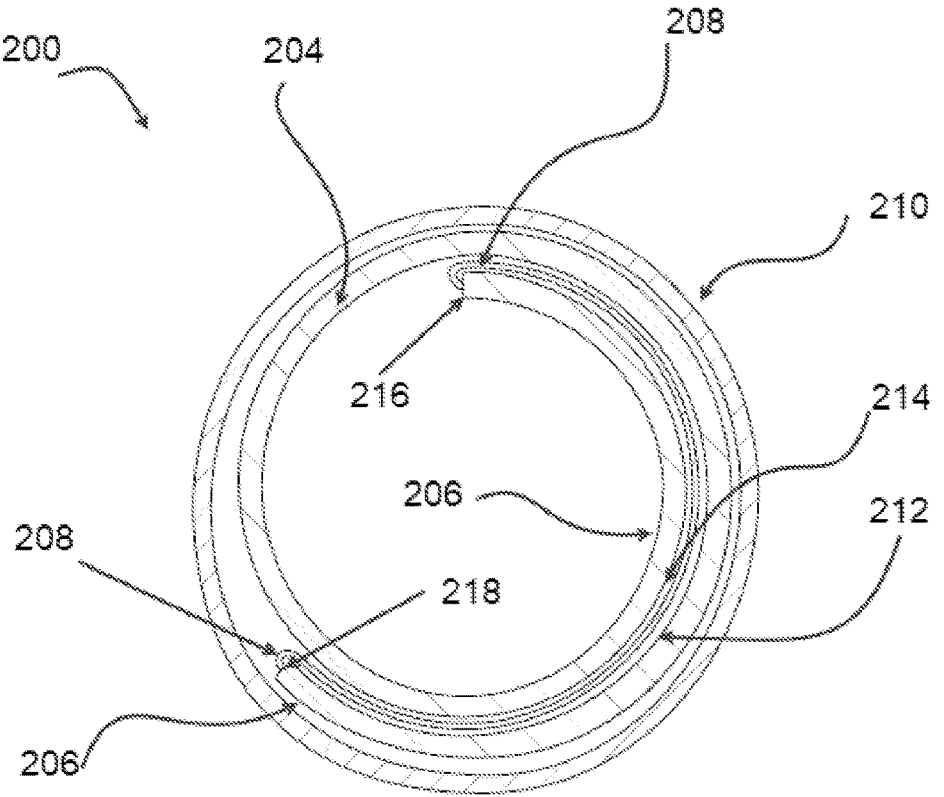
FIG. 2B shows a cross-section view of the unexpanded sheath depicted in FIG. 2A.

FIGS. 2A and 2B show schematics of an unexpanded sheath in some of the disclosed herein aspects for use with a delivery apparatus such as that shown in FIG. 1. FIG. 2A shows a perspective of the unexpanded sheath 200 comprising an inner layer 202, wherein the inner layer comprises a reinforcing layer 204 and a polymer layer 206. In this exemplary and unlimiting aspect, for illustration purposes only, the terminal part of the reinforcing layer 204 is shown not to be encapsulated within the polymer layer 206. However, it is also understood that in some exemplary and unlimiting aspects, a distal part of the sheath and/or proximal part of the sheath can comprise a reinforcing layer that extends beyond the polymer layer and is not encapsulated within the polymer layer. FIG. 2B shows a cross-sectional view of the sheath 200, wherein the reinforcing layer 204 is encapsulated within the polymer layer 206, and a tether portion 208 is also formed.

As disclosed herein, and as shown in FIG. 2B, the polymer layer 206 extends circumferentially to the reinforcing layer 204 such that the reinforcing layer is substantially encapsulated within at least a portion of the polymer layer 206. It can be further seen that the polymer layer 206 comprises a tether portion 208 that is substantially free of the reinforcing layer. The reinforcing layer 204, encapsulated into the polymer layer 206, is rolled into a spiral configuration such that at least a portion of the inner surface 212 of the encapsulated reinforcing layer overlays at least a portion of the outer surface 214 of the reinforcing layer to form an overlapping portion of the spiral configuration. In such exemplary aspects, a first longitudinal edge 216 of the encapsulated reinforcing layer 204 is slidable along at least a portion of the inner surface 212 of the encapsulated reinforcing layer 204, and a second longitudinal edge 218 is slidable along at least a portion of the outer surface 214 of the encapsulated reinforcing layer 204 to increase or decrease the overlapping portion of the spiral configuration.

Sheath, as shown in FIG. 2A and FIG. 2B can further include an outer layer 210.

The inner layer 202 defines a lumen 220 through which a delivery apparatus can travel into a patient's vessel in order to deliver, remove, repair, and/or replace a prosthetic device. The disclosed sheath can also be useful for other types of minimally invasive surgery, such as any surgery requiring introducing an apparatus into a subject's vessel. For example, the disclosed sheath also can be used to introduce other types of delivery apparatus for placing various types of intraluminal devices (e.g., stents, stented grafts, etc.) into many types of vascular and non-vascular body lumens (e.g., veins, arteries, esophagus, ducts of the biliary tree, intestine, urethra, fallopian tube, other endocrine or exocrine ducts, etc.).

Figures 3A, 3B:
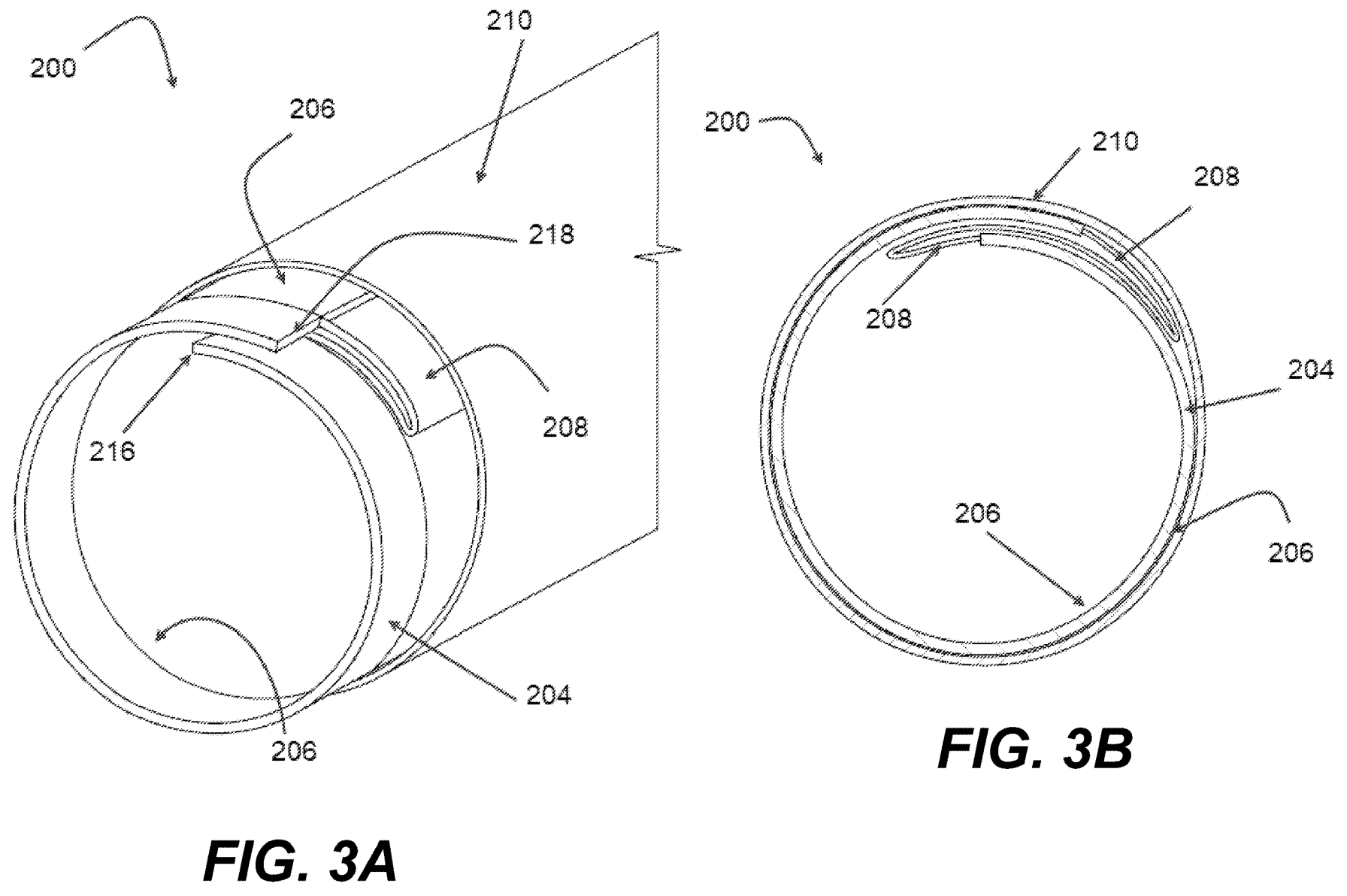

FIGS. 3A and 3B depict the exemplary sheath 200, as described in the aspects herein, present in an expanded configuration. It can be seen that upon expansion, the first longitudinal edge 216 slides along at least a portion of the inner surface of the encapsulated reinforcing layer 204, and the second longitudinal edge 218 slides along at least a portion of the outer surface of the encapsulated reinforcing layer 204 thereby decreasing the overlapping portion of the spiral configuration.

In some aspects, when the sheath is in an unexpanded state, the overlapping portion can comprise about 30% to about 70% of a reinforcing layer width, including exemplary values of about 31%, about 32%, about 33%, about 34%, about 35%, about 36%, about 37%, about 38%, about 39%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, and about 69%. It is understood that the reinforcing layer width, as described herein, is a reinforcing layer width measured prior to rolling the reinforcing layer into the spiral configuration.

In yet other aspects, when the sheath is in the expanded state, the overlapping portion can comprise about 10% to about 20% of a reinforcing layer width, including exemplary values of about 11%, about 12%, about 13%, about 14%, about 15%, about 16%, about 17%, about 18%, and about 19%. It is understood that the reinforcing layer width, as described herein, is a reinforcing layer width measured prior to rolling the reinforcing layer into the spiral configuration. In yet other exemplary and unlimiting aspects (not shown), the first and the second portions can slide to arrive at a configuration where the first longitudinally extending edge is abut or in near proximity to the second longitudinally extending edge, substantially reducing or substantially eliminating the overlapping portion of the sheath.

Figure 3C:
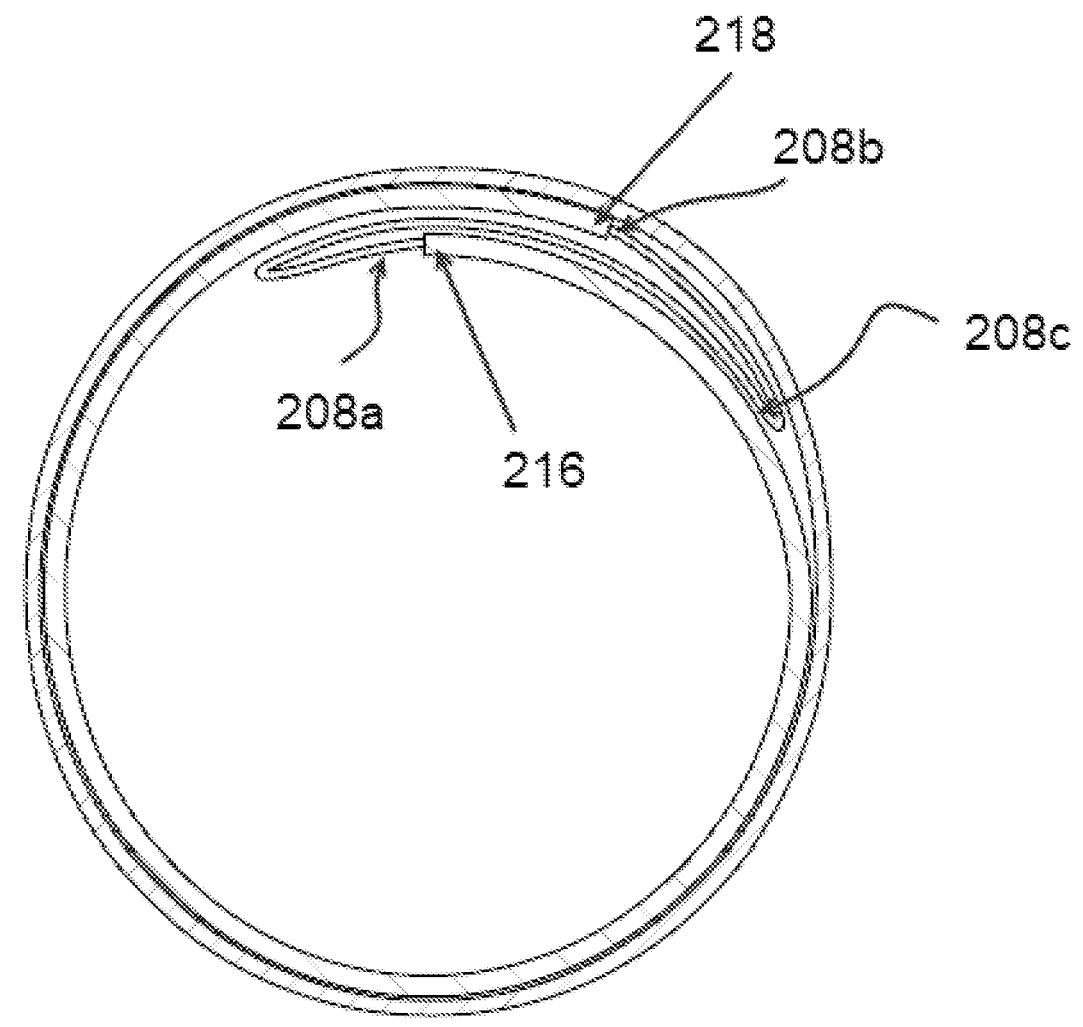
FIG. 3C shows a depiction of the tethered portion.
Figure 4A:
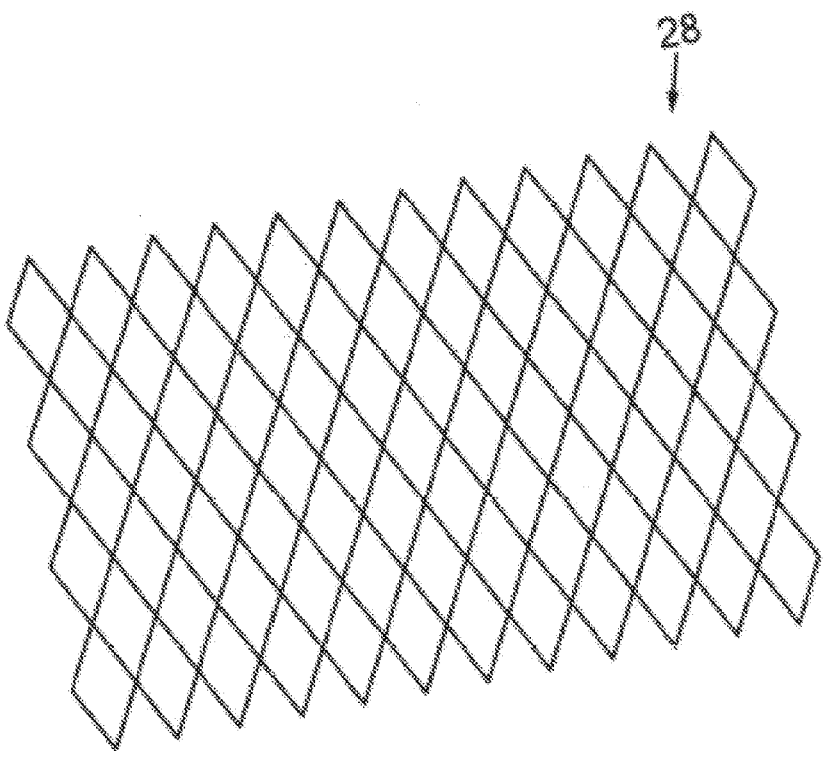
FIGS. 4A-4F depict various exemplary patterns of a reinforcing layer in some exemplary aspects.
Figure 4B:
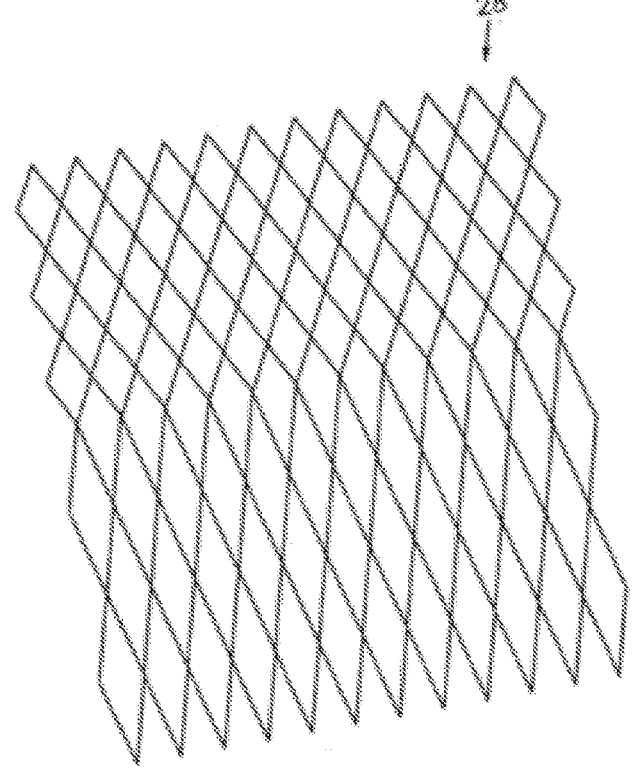
Figure 4C:
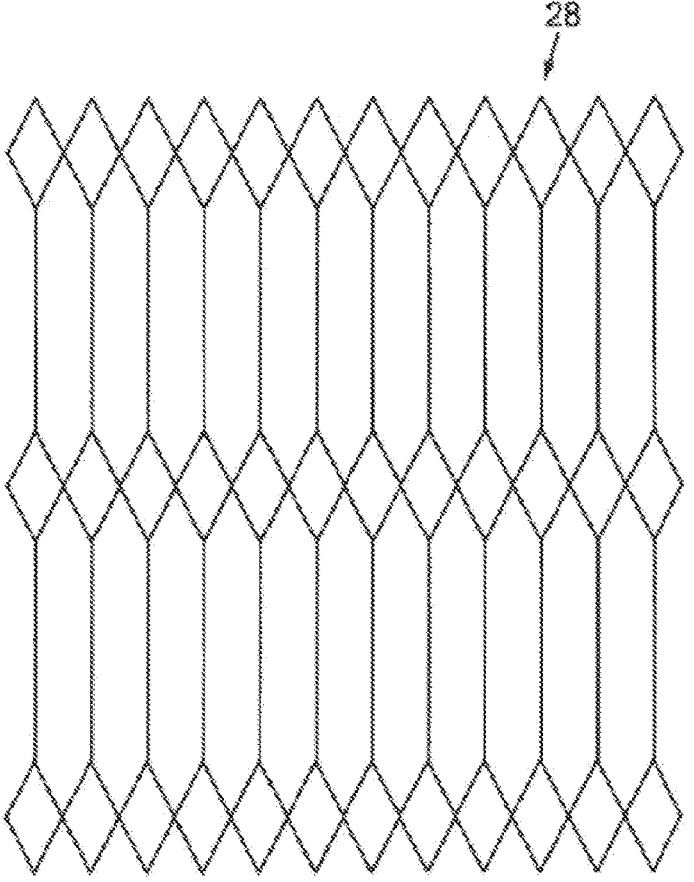
Figure 4D:
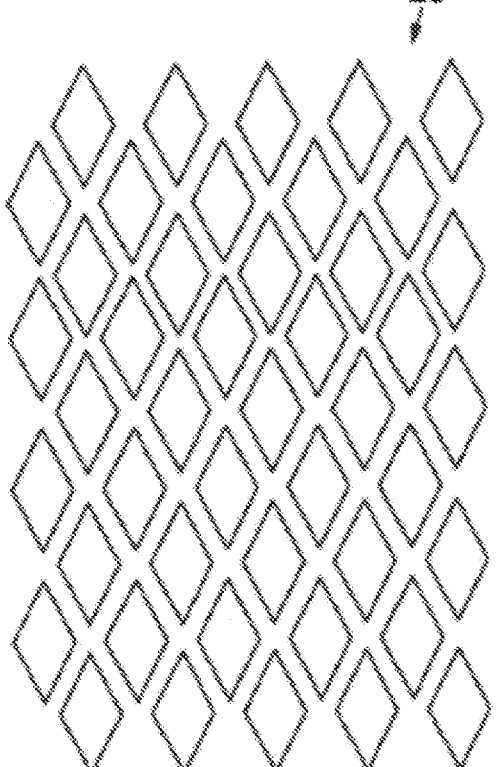
Figure 4E:
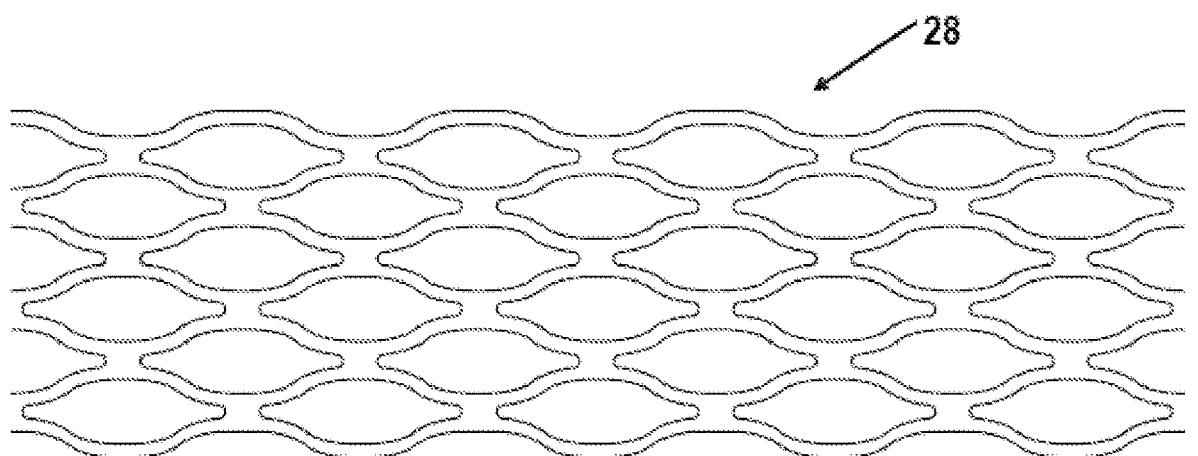
Figure 4F:
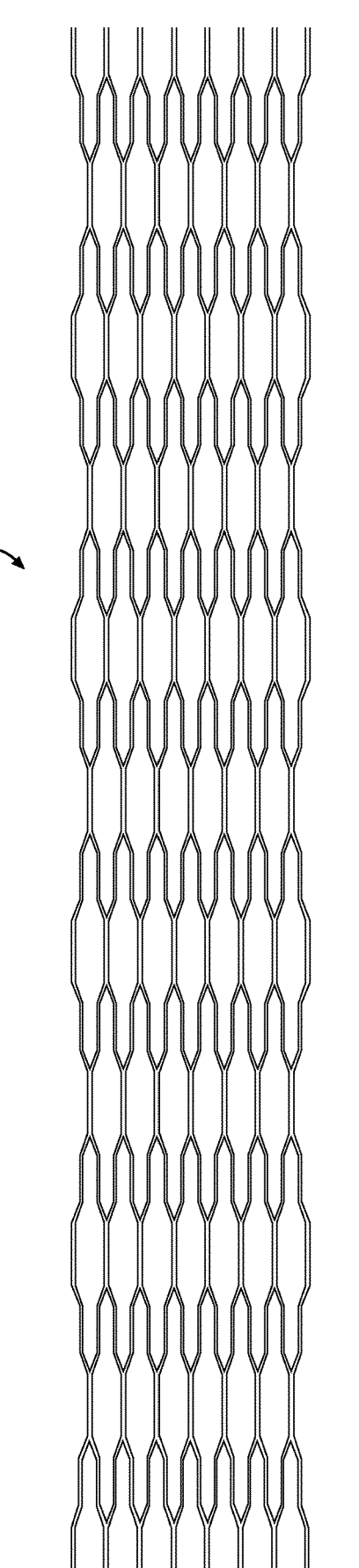

In still further aspects, and as shown in FIG. 3C, the tether portion can comprise a first portion of the polymer 208a that extends beyond the first edge 216 of the reinforcing layer, a second portion 208b that extends beyond the second edge 218 of the reinforcing layer, and a third portion 208c that extends between the first portion 208a and the second portion 208b. As can be further seen in FIG. 3C, the first, the second, and the third portions of the tether portion of the polymer layer can form at least one fold that is at least partially positioned within the overlapping portion of the spiral configuration.

It is understood that aspects disclosed herein can comprise a reinforcing layer formed of any material that can provide for the desired stiffness and is capable to provide reinforcing properties to the sheath. In certain aspects, the reinforcing layer comprises a metal or a polymer, or a combination thereof.

In some aspects, the polymer can comprise any hard plastic. In still further aspects, the polymer can comprise PEEK, nylon, or a combination thereof. In still further aspects, the polymer can have any modulus that provides for the desired stiffness profile. In certain aspects, the polymer can exhibit modulus from about 1 GPa to about 10 GPa, including exemplary values of about 2 GPa, about 3 GPa, about 4 GPa, about 5 GPa, about 5 GPa, about 6 GPa, about 7 GPa, about 8 GPa, and about 9 GPa.

In yet further aspects, the polymer can be a solid polymeric sheet of the desired thickness. Yet, in other aspects, it can be an etched or a cut polymeric sheet.

In certain aspects, the metal can be a solid metallic sheet of the desired thickness. However, yet in other aspects, the reinforcing layer can be a metallic etched sheet. In such a metallic etched sheet, various patterns can be formed using any known in the art etching process, including solution etching, photoetching, plasma etching, etc. In yet further aspects, the reinforcing layer can be a metallic laser-cut sheet. In such exemplary and unlimiting aspects, the metallic sheet is laser cut to create any desired patterns.

In yet still further aspects, the reinforcing layer can be a metallic tube that can be laser cut to create the desired pattern and then longitudinally cut to form the first longitudinally extending edge and the second longitudinally extending edge. In such exemplary and unlimiting aspects, the metallic laser-cut tube can be a hypotube.

In still further aspects, the reinforcing layer can be formed from a composite material that comprises both a metal and a polymer.

In yet other aspects, the reinforcing layer can have a thickness from about 0.001" to about 0.020" including exemplary values of about 0.002" about 0.003", about 0.004", about 0.005", about 0.006", about 0.007", about 0.008", about 0.009", about 0.010", about 0.011", about 0.012", about 0.013", about 0.014", about 0.015", about 0.016", about 0.017", about 0.018", and about 0.019".

It is further understood that the reinforcing layer can be formed by any known in the art methods. In certain aspects, the first and the second longitudinally extending edges are substantially straight. However, also disclosed herein are aspects where the first longitudinally extending edge is straight, while the second longitudinally extending edge can have any non-straight geometry. Similarly, also disclosed are aspects where the first longitudinally extending edge comprises any known non-straight geometry, while the second longitudinally extending edge is substantially straight. In yet further aspects, both the first and the second longitudinally edges can have any known in the art non-straight geometries. It is understood that in such an exemplary aspect, the not-straight geometry of the first and the second longitudinally extending edges can be the same or different. Even further, it is understood that the geometry of each edge can vary across a length of the sheath and can comprise both straight and various non-straight geometries along the first and/or the second edge along various portions of the sheath.

In still further aspects, the first and/or the second longitudinally extending edges can be helically wrapped such that their seam follows a circuitous path about the central axis of the sheath. Accordingly, in such exemplary and unlimiting aspects, the expansion can occur along this helical seam during introduction of a valve or interior catheter rather than in a purely longitudinal orientation.

In still further aspects, the reinforcing layer can comprise a cut, or an etch pattern that can have any known in the art shape. For example, and without limitation, the reinforcing layer can comprise a cut, or an etch pattern having a regular or irregular shape. In yet other aspects, the cut and/or the etch pattern can be repetitive. In such exemplary aspects, the repetitions can be random or structured. In yet other aspects, the reinforcing layer can have various patterns that are not necessarily repetitive.

In still further aspects, the cut pattern can comprise a c-cut, a diamond-cut, a spiral cut, an interrupted cut, or any combination thereof. In certain aspects, a cut or an en etch pitch, a cut and etch density of the cut, or the etch pattern can vary along a length of the reinforcing layer to incorporate various stiffness profiles to achieve the desired properties of the sheath. The desired properties can include by are not limited to being substantially kink-resistant or provide a stiffness that allows passage of the medical device without damaging the surrounding tissues. It is further understood that the reinforcing layer is configured to provide the torquability of the sheath during the insertion of the prosthetic device.

In certain aspects, and as described herein, when the reinforcing layer is metallic, the layer comprises a metal having a modulus from about 20 GPa to about 250 GPa, including exemplary values of about 50 GPa, about 60 GPa, about 70 GPa, about 80 GPa, about 90 GPa, about 100 GPa, about 110 GPa, about 120 GPa, about 130 GPa, about 140 GPa, about 150 GPa, about 160 GPa, about 170 GPa, about 180 GPa, about 190 GPa, about 200 GPa, about 210 GPa, about 220 GPa, about 230 GPa, and about 240 GPa to achieve the desired predetermined stiffness profile. In yet other aspects, the metal used to form the reinforcing layer can comprise a titanium metal or its alloys, nitinol, stainless steel, cobalt-chromium alloy, or any combination or alloys thereof.

In yet further aspects, the reinforcing layer can comprise a plurality of enclosed interstices formed by the cut or the etch pattern. Exemplary patterns that can be present in the reinforcing layer 28 are shown in FIGS. 4A-4F. It is understood that the pattern of the reinforcing layer 28 can vary from section to section, changing along the length of the sheath. It is further understood that the structures shown in FIGS. 4A-F are not necessarily drawn to scale and show just exemplary and unlimiting aspects. It is further understood that the reinforcing layer can have any stent-like pattern.

Figure 5A:
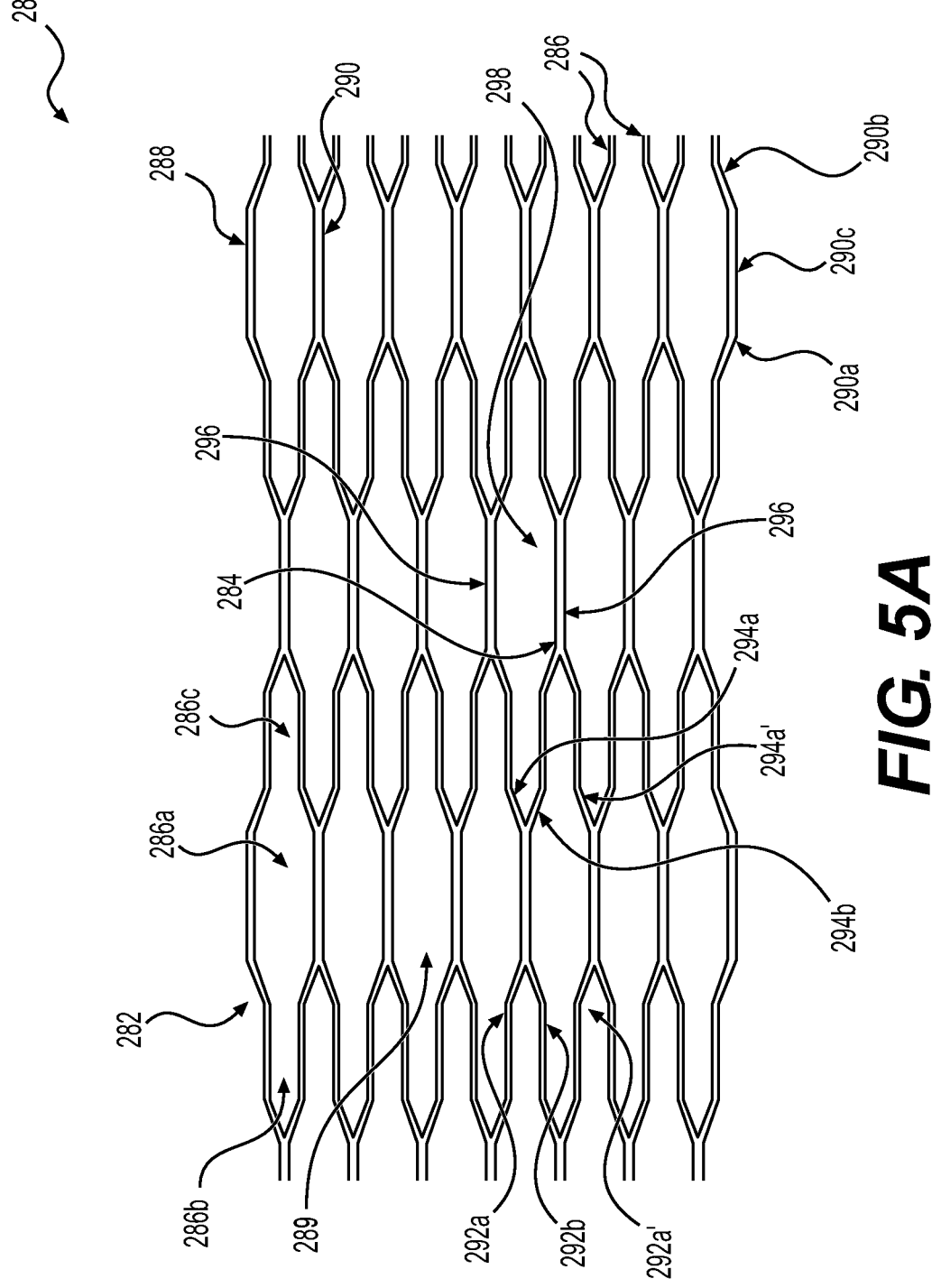
FIGS. 5A-5B depict various exemplary patterns of a reinforcing layer in other exemplary aspects.

In some exemplary and unlimiting aspects, and as shown in FIG. 5A, the reinforcing layer 28 can comprise a repetitive cut or etch pattern 282 arranged in a plurality of radial rows, wherein each row comprises a plurality of struts 286 forming a first plurality of enclosed interstices 289, wherein each of the plurality of enclosed interstices has a central portion 286*a*, an enclosed first end portion 286*b* and an enclosed second end portion 286*c*, wherein the central portion of the interstice has a first width, the first end portion of the interstice has a second width, and the second end portion of the interstice has a third width. It is understood that in some aspects, the second width can be substantially identical to the third width. While in yet other aspects, the second and the third width can be different. In still further aspects, the first width can be greater than the second and the third widths.

In certain and unlimiting aspects, the central portion comprises a first strut 288 and an opposite second strut 290, and wherein two abut interstices share at least a portion of the first strut or the second strut. As further can be seen in FIG. 5A, each of the first and the second struts has a first end and a second end and a straight portion extending between the first end and the second end (as shown, for example, for the second strut 290, 290*a*-290*c*, respectively). In certain and unlimiting aspects, each of the first and the second struts can split at the first end into a first arm 292*a* and a second arm 292*b*, for example, in a first slingshot configuration and at the second end into a third arm 294*a* and a fourth arm 294*b*, for example, in a second slingshot configuration. It is understood that the second arm 292*b* of the first strut and the first arm 292*a*' of the second strut can gather to form an enclosed first end portion, while the fourth arm 294*b* of the first strut and the third arm 294*a*' of the second strut gather to form the enclosed second portion.

As shown in FIG. 5A, at a gathering point 284, the second arm of the first strut and the first arm of the second strut extend into a first bridging member 296 in a slingshot configuration connecting between the first end portion of the interstice in one row and a second end portion of the interstice in a row below.

Similarly, at a gathering point, the fourth arm of the first strut and the third arm of the second strut extend into a second bridging member connecting the second end portion of the interstice in one row and a first end portion of the interstice in a row above. Even further, for example, two of the first bridging members 296 of each of two abut interstices can form a second plurality of enclosed interstices 298 between one row and the row below. Similarly, two of the second bridging members of each of two abut interstices can form a third plurality of enclosed interstices between one row and the row above.

It is understood that in some aspects, the thickness of each of the struts can have any value that provides for the desired properties of the reinforcing layer. In certain aspects, the thickness of each of the plurality of struts is the same. Yet on other aspects, it can be different. In certain aspects, a thickness of the straight portion of the first and the second struts can be greater than a thickness of the first, second, third, or fourth arms.

Figure 5B:
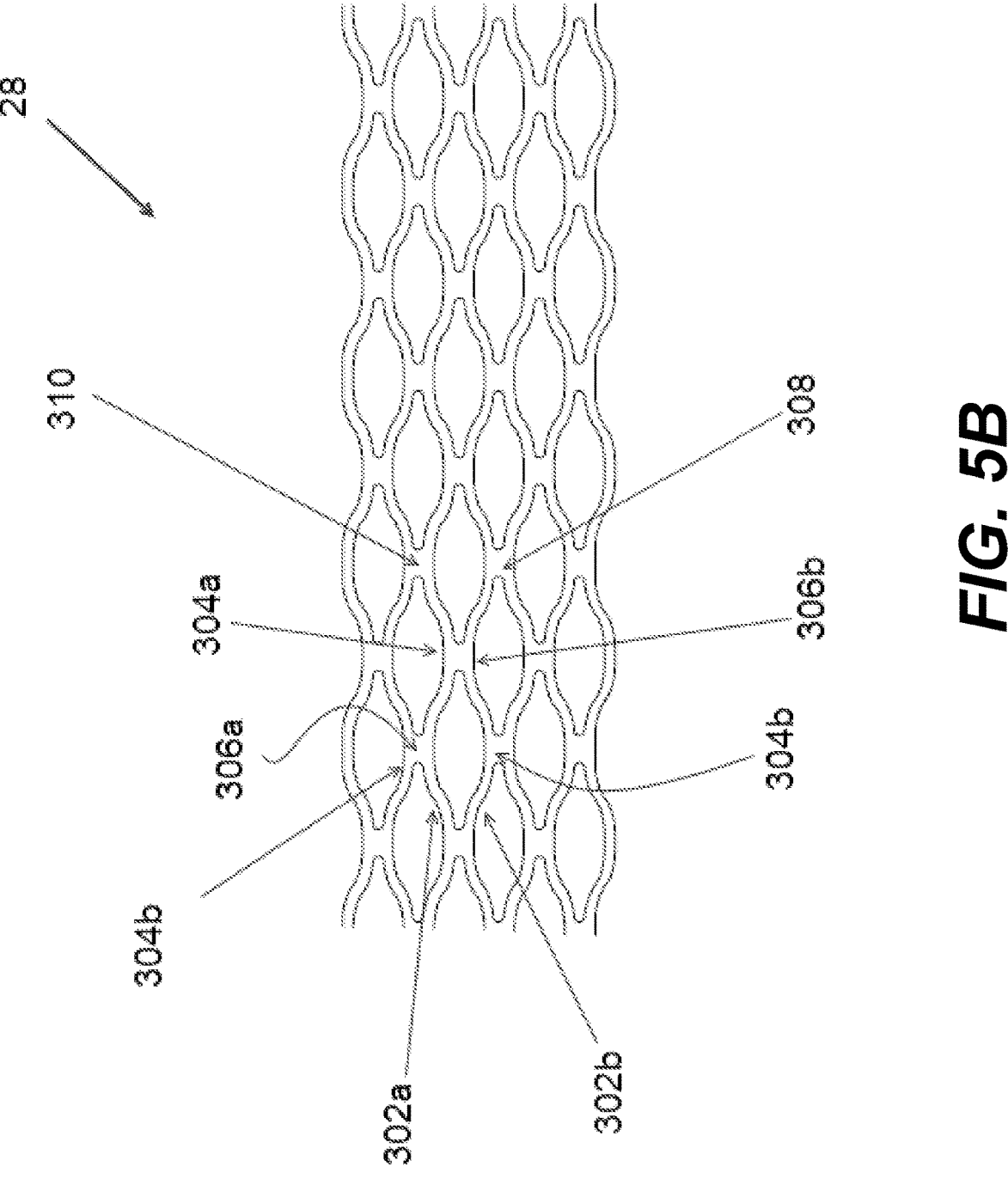

FIG. 5B shows an additional aspect where the reinforcing layer 28 comprises a plurality of longitudinally undulating struts 302*a* and 302*b*, for example, wherein the undulating struts form a plurality of consecutive valleys 304*a* and 304*b* and apexes 306*a* and 306*b*. In such exemplary aspects, two longitudinally adjacent struts (302*a* and 302*b*) have an opposite undulation phase such that each of the plurality of valleys of a first strut 304*a* is proximal to each of the apexes of a first adjacent strut 306*b*, and wherein each of the apexes of the first strut 306*a* is proximal to each of the plurality of valleys 304*b* of a second adjacent strut.

In still further aspects, a first bridge member 308 extends from at least a portion of the each of the plurality of valleys of the first strut to at least a portion of the each of the apexes of the first adjacent strut and wherein a second bridge member 310 extends from at least a portion of the each of the apexes of the first strut to at least a portion of the each of the plurality of valleys of the second adjacent strut, thereby forming rows of enclosed interstices between every two adjacent struts.

Figure 6:
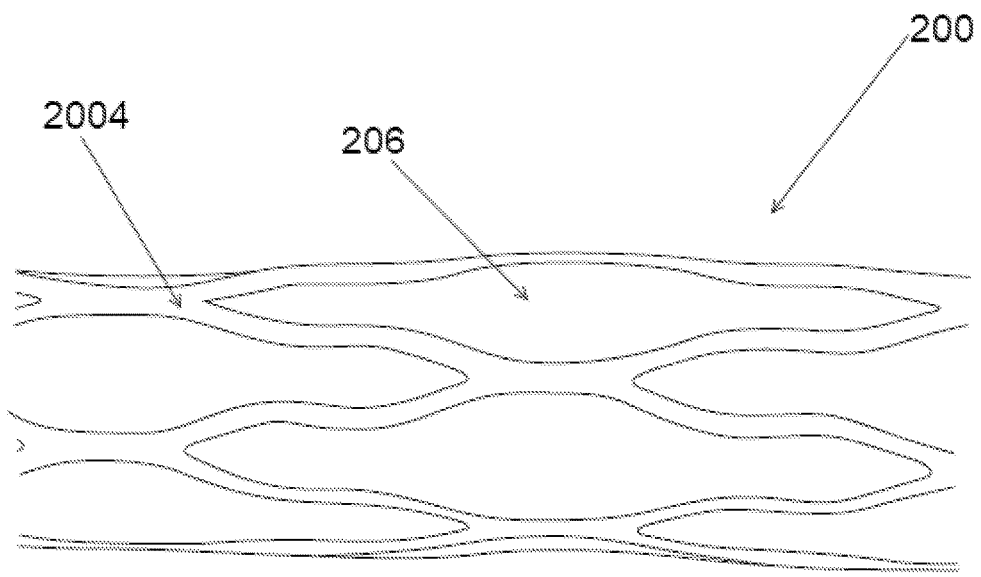
FIG. 6 shows a top view of a reinforcing layer encapsulated into a polymer layer in one aspect.

FIG. 6 shows a top view of the inventive sheath 200 in another aspect, that shows an encapsulated in the polymer layer reinforcing layer 2004, and a polymer layer 206 filling the plurality of interstices of the reinforcing layer.

Figure 7:
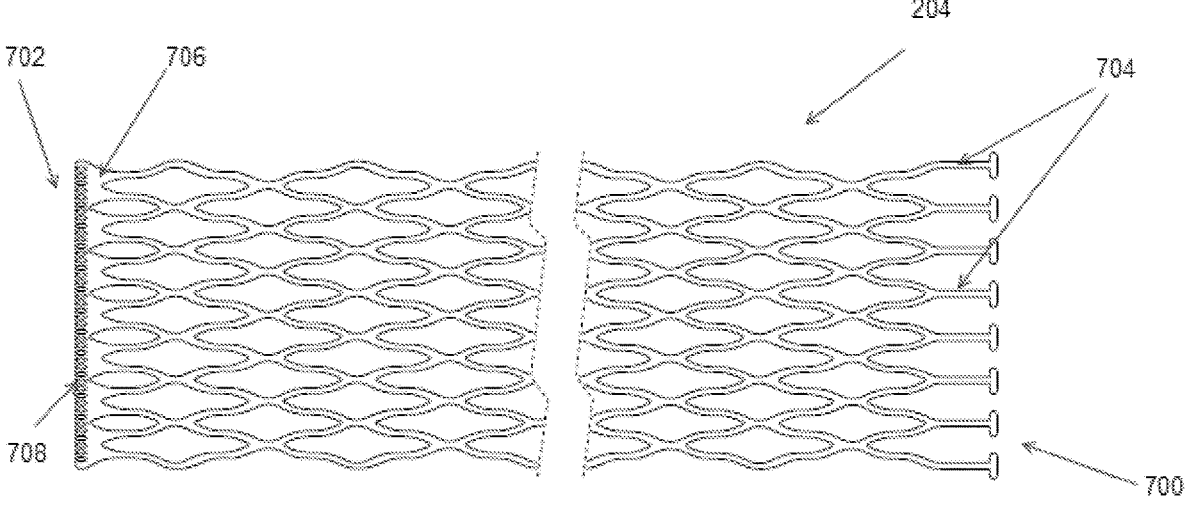
FIG. 7 depicts a planar view of various configurations of a reinforcing layer in various aspects.
Figure 9:
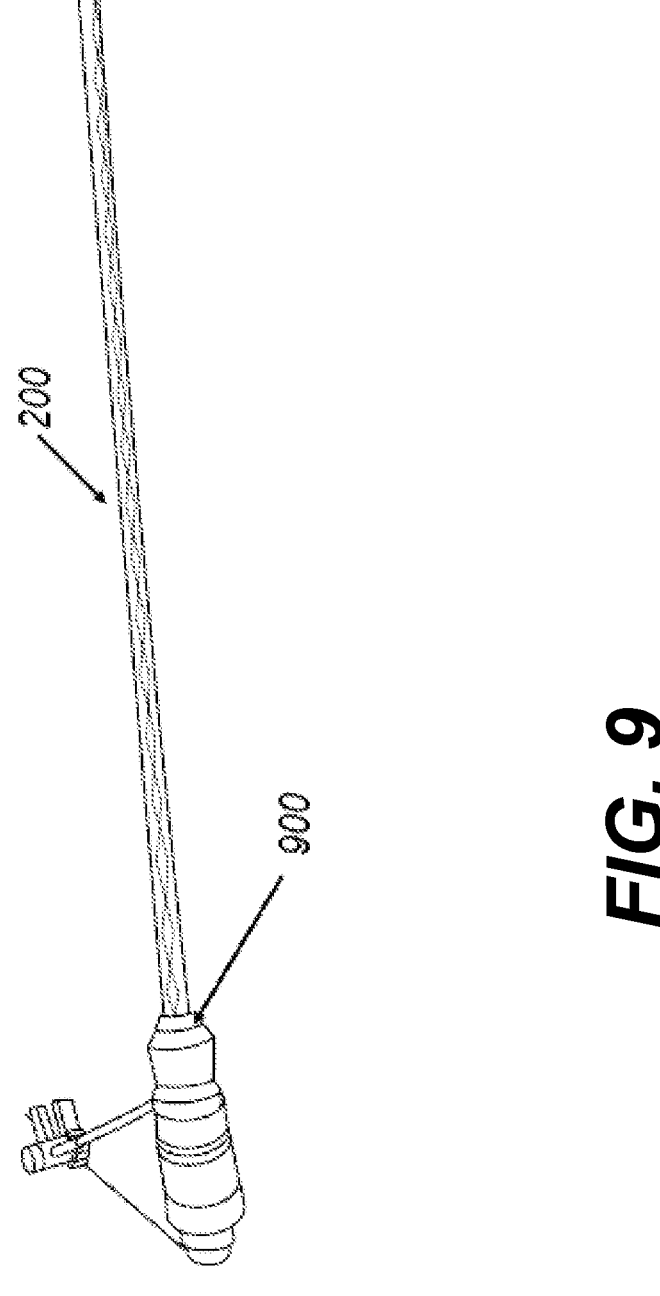
FIG. 9 depicts an exemplary sheath connected to a hub.

In still further aspects, the reinforcing layer can be uniform along a longitudinal axis of the sheath. While in some other aspects, the reinforcing layer can vary along a longitudinal axis of the sheath. Referring to FIG. 7, it shows an exemplary planar (not rolled into a spiral configuration) reinforcing layer having a proximal end 700 and a distal end 702. In certain exemplary aspects, the distal end 702 of the reinforcing layer can differ from the proximal end 700 of the reinforcing layer. For example, the reinforcing layer 204 can comprise a plurality of extension struts 704 configured to secure the reinforcing layer to a hub. In certain aspects, the plurality of extension struts can be further flared out radially to ensure a better coupling to the hub. FIG. 9 shows an exemplary sheath 200 connected to a hub 900.

In some aspects, the plurality of extension struts 704 can have a T-bar shape (for example, shown in FIG. 7), or it can have an island shape (not shown).

In yet other aspects, the distal end 702 of the reinforcing layer comprises an enclosed distal end portion 706 connecting all enclosed interstices present proximally to the enclosed distal end portion. In yet further aspects, the enclosed distal end portion can further comprise a plurality of reflow features 708 configured to integrally connect the distal end of the reinforcing layer with a tip of the sheath.

In still further aspects, the polymer layer disclosed herein can comprise any polymers known in the art and suitable for the desired application. It is understood that in some aspects, the polymer layer is lubricious. In such exemplary and unlimiting aspects, the polymer layer has a friction coefficient of about 0.1 or less, of about 0.09 or less, about 0.08 or less, about 0.07 or less, about 0.05 or less, about 0.04 or less, about 0.03 or less, about 0.02 or less, or about 0.01 or less.

In yet further aspects, the polymer layer is substantially not stretchable. In certain aspects, the polymer layer can comprise ePTFE, PTFE, polyethylene, ultrahigh molecular weight polyethylene (UHMWPE) (such as Dyneema®), polyvinylidene fluoride, and combinations thereof.

In still further aspects, the polymer layer can comprise one or more sublayers. In some aspects, if one or more sublayers are present, each sublayer can comprise the same or different polymer. In yet further aspects, the encapsulation of the reinforcing layer with the polymer layer can be done by a sintering process.

In still further aspects, a combined thickness of the polymer layer and the reinforcing layer is from about 0.003" to about 0.030", including exemplary values of about 0.004", about 0.005", about 0.006", about 0.007", about 0.008", about 0.009", about 0.010", about 0.011", about 0.012", about 0.013", about 0.014", about 0.015", about 0.016", about 0.017", about 0.018", about 0.019", about 0.020", about 0.021", about 0.022", about 0.023", about 0.024", about 0.025", about 0.026", about 0.027", about 0.028", and about 0.029".

In still further aspects, a thickness of the polymer layer within the plurality of enclosed interstices can be from less than about 0.001" to about 0.030" including exemplary values of about 0.0001", about 0.0002", about 0.0003", about 0.0004", about 0.0005", about 0.0006", about 0.0007", about 0.0008", about 0.0009", about 0.001", about 0.002", about 0.003", about 0.004", about 0.005", about 0.006", about 0.007", about 0.008", about 0.009", about 0.010", about 0.011", about 0.012", about 0.013", about 0.014", about 0.015", about 0.016", about 0.017", about 0.018", and about 0.019", about 0.020", about 0.021", about 0.022", about 0.023", about 0.024", about 0.025", about 0.026", about 0.027", about 0.028", about 0.029", about 0.030", about 0.031", about 0.032", about 0.033", about 0.034", about 0.035", about 0.036", about 0.037", about 0.038", and about 0.039".

In still further aspects and as disclosed herein, the sheath can also comprise an outer layer. In certain aspects, the outer layer can be an elastomeric material. In yet further aspects, the outer layer can extend all the way from the proximal end of the sheath to the distal end of the sheath. While in some exemplary and unlimiting aspects, the outer layer can extend only partway from the proximal end of the sheath. The outer cover is positioned to surround the entire circumference of the inner layer and comprises any known in the art pliable, elastic material(s) that can expand and contract. In some aspects, the outer layer can have a high expansion ratio.

The outer layer comprising an elastomeric material can, in some aspects, provide hemostasis (e.g., prevent blood loss during implantation of the prosthetic device). For example, the outer layer 210 can be sized or configured to form a seal with the patient's artery when inserted, such that blood is substantially prevented from flowing between the outer layer 210 and the vessel wall. The outer layer 210 can be inserted such that it passes the arteriotomy.

In such aspects, the elastomeric outer layer can comprise any suitable materials, such as any suitable heat shrink materials. In yet other aspects, the outer layer comprises a compound comprising a heat shrinking material, a polyether block amide, a polyurethane, silicone, polyisoprene, or any combination thereof present up to 100 wt %, including exemplary values of about 1 wt %, about 10 wt %, about 20 wt %, about 30 wt %, about 40 wt %, about 50 wt %, about 60 wt %, about 70 wt %, about 80 wt %, about 90 wt %, and 100 wt % based on a total weight of the compound. In yet further exemplary aspects, the outer layer comprises PEBAX®.

In still further aspects, the outer layer can also comprise a styrene-based elastomer, polyurethane, latex, copolymers thereof, blends thereof, or co-extrudates of thereof. In certain and unlimiting aspects, the elastomeric polymer can comprise polyether block ester copolymer, polyesters, poly-vinyl chloride, thermoset silicone, poly-isoprene rubbers, polyolefin, other medical grade polymers, or combinations thereof. In yet further aspects, the elastomeric polymer described herein can have any useful additives. In certain aspects, the elastomeric polymers can comprise at least one friction reduction additive. In some exemplary aspects, the friction reduction additives can comprise, for example, BaSO4, ProPell™, PTFE, any combination thereof, and the like. It is understood that this list of friction reduction additives is not limiting, and any known in the art friction reductions additives can be utilized.

In still further aspects, the outer layer can have a Shore hardness of from about 25 Durometer to about 90 Durometer, including exemplary values of about 30 Durometer, about 40 Durometer, about 45 Durometer, about 50 Durometer, about 55 Durometer, about 60 Durometer, about 65 Durometer, about 70 Durometer, about 75 Durometer, about 80 Durometer, and about 85 Durometer.

It is understood that in some aspects, the outer layer can have the same Shore hardness along a length of the sheath. In yet other aspects, the Shore hardness of the polymer layer can vary along a length of the sheath. For example, and without limitation, disclosed herein are aspects where a durometer of the outer layer at the proximal end of the sheath can be different from a durometer of the outer layer at the distal end of the sheath.

In still further aspects, the outer layer can comprise various polymer layers. In some aspects, the outer layer can comprise the first polymer layer, having a first compound composition comprising from greater than 0 wt % to less than 100 wt %, including exemplary values of about 0.01 wt %, about 1 wt %, about 5 wt %, about 10 wt %, about 15 wt %, about 20 wt %, about 25 wt %, about 30 wt %, about 35 wt %, about 40 wt %, about 45 wt %, about 50 wt %, about 55 wt %, about 60 wt %, about 65 wt %, about 70 wt %, about 75 wt %, about 80 wt %, about 85 wt %, about 90 wt %, about 95 wt %, and about 99.9 wt % of a polymer comprising a polyether block amide, a polyurethane, or any combination thereof.

In still further aspects, the first compound composition can comprise from greater than about 35 wt % to less than about 80 wt %, including exemplary values of about 40 wt %, about 45 wt %, about 50 wt %, about 55 wt %, about 60 wt %, about 65 wt %, about 70 wt %, and about 75 wt % of a polymer comprising a polyether block amide, a polyure-thane, or any combination thereof.

In certain aspects, the polymer in the first compound composition comprises a polyether block amide. In such exemplary aspects, the polyether block amide can comprise PEBAX® from Arkema. In yet further aspects, the polymer can comprise polyurethane, for example, NEUSoft⬚ . While in still further aspects, the polymer can compromise a combination of the polyether block amide, such as, for example, PEBAX® and polyurethane. It is further understood that if the mixture of the polymers is present, such a mixture can comprise each component in any amount relative to another component to provide the desired polymer falling within the disclosed above range.

In still further aspects, the first compound composition can comprise less than about 65 wt % of an inorganic filler based on a total weight of the first compound composition, including exemplary values of less than about 60 wt %, less than about 55 wt %, less than about 50 wt %, less than about 45 wt %, less than about 40 wt %, less than about 35 wt %, less than about 30 wt %, less than about 25 wt %, less than about 20 wt %, less than about 15 wt %, less than about 10 wt %, less than about 5 wt %, and less than about 1 wt % of the inorganic filler.

In yet further aspects, the inorganic filler can be present in an amount of at least about 1 wt %, at least about 2 wt %, at least about 5 wt %, at least about 10 wt %, at least about 15 wt %, at least about 20 wt %, at least about 25 wt %, at least about 30 wt %, at least about 35 wt %, at least about 40 wt %, at least about 45 wt %, at least about 50 wt %, or at least about 55 wt %.

In still further aspects, the inorganic filler can comprise any inorganic materials that can be used as a filler and are acceptable for the desired application. In certain exemplary and unlimiting aspects, the inorganic filler can comprise bismuth oxychloride, barium sulfate, bismuth subcarbonate, calcium carbonate, aluminum trihydrate, barite, kaolin clay, limestone, or any combination thereof. Again it is under-stood that the inorganic filler can comprise a combination of the various fillers. In such exemplary aspects, an amount of each filler in the combination can be in any range to provide a final combination that falls within the disclosed above range.

In still further aspects, the first compound composition can comprise up to about 20 wt % of a solid lubricant filler based on a total weight of the first compound composition, including exemplary values of about 0.01 wt %, about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, and about 19.9 wt %. In yet further aspects, the solid lubricant filler can be present up to about 20 wt %, up to about 15 wt %, or up to about 10 wt % based on a total weight of the first compound composition.

In still further aspects, the solid lubricant filler can comprise any additive that is known to reduce friction and behave as a lubricant. In such exemplary and unlimiting aspects, the solid lubricant filler can comprise one or more of graphene, reduced graphene oxide, carbon black, boron nitride, silicones, talc, polytetrafluorethylene (PTFE), fluorinated ethylene propylene, and the like. In still further aspects, the solid lubricant comprises a PTFE filler. In yet further aspects, the PTFE filler is a powder.

In still further aspects, the first compound composition can further comprise at least one tackiness reducing compound. Any compounds known in the art as capable of reducing the tackiness of the polymer composition can be considered and used for the purpose of this disclosure. In yet further exemplary and unlimiting aspects, the at least one tackiness reducing compound comprises ProPell™ from Foster Corporation In certain aspects, the at least one tackiness reducing compound is present in an amount from 0 wt % to about 20 wt %, including exemplary values of about 0.01 wt %, about 0.05 wt %, about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, and about 19 wt % based on a total weight of the first compound composition. In still further aspects, the at least one tackiness reducing compound is present in any amount having a value between any two foregoing values. For example, and without limitation, the at least one tackiness reducing compound can be present in an amount from about 1 wt % to about 5 wt %, or from about 5 wt % to about 10 wt % based on a total weight of the first compound composition.

Yet, in other aspects, two or more polymer layers can be present in the outer layer. In such exemplary aspects, the outer layer can comprise at least one second polymer layer comprising a second compound composition. It is understood that the second compound composition can be the same or different. It can comprise the same or different inorganic fillers, solid lubricants, and optionally tackiness reducing agents. In yet other aspects, the second compound composition does not comprise inorganic fillers, solid lubricants, and/or tackiness reducing agents. In still further aspects, each layer present in the outer layer can have the same or different Shore hardness.

It is further understood that in certain aspects, the first polymer in the first compound composition can be the same as the second polymer in the second compound composition. Yet, in other aspects, the first polymer in the first compound composition is different from the second polymer in the second compound composition. In yet further aspects, the second polymer layer composition comprises PEBAX®. While in further aspects, the second polymer layer composition can comprise polyurethane, for example, NEUSoft® from PolyOne.

In still further aspects, and as disclosed herein, the outer layer has a predetermined thickness, and wherein at least about 10%, at least about 20%, at least about 30%, at least about 40%, at least about 50%, at least about 60%, at least about 70%, at least about 80%, at least about 90%, or 100% of the predetermined thickness comprises the first and/or the second compound composition comprising the first and/or the second polymer having a Shore D equal to or lower than about 30 D.

The outer layer can have a thickness ranging from, for example, about 0.001" to about 0.010", including exemplary values of about 0.002", about 0.003", about 0.004", about 0.005", about 0.006", about 0.007", about 0.008", and about 0.009".

In still further aspects, the thickness of the outer layer can vary along a length of the sheath. Yet, in further aspects, the thickness of the outer layer is greater at the proximal end.

In still further aspects, if, for example, two polymer layers are present in the outer layer, each of the polymer layers can have the same thickness. While in other aspects, the first polymer layer and the second polymer layer have a different thicknesses. For example, in some aspects, the first polymer layer has a thickness of about 0.001" to about 0.003", including exemplary values of about 0.0011", about 0.0012", about 0.0013", about 0.0014", about 0.0015", about 0.0016", about 0.0017", about 0.0018", about 0.0019", about 0.002", about 0.0021", about 0.0022", about 0.0023", about 0.0024", about 0.0025", about 0.0026", about 0.0027", about 0.0028", and about 0.0029". Yet still, in further aspects, the second polymer layer can have a thickness of about 0.002" to about 0.004", including exemplary values of about 0.0021", about 0.0022", about 0.0023", about 0.0024", about 0.0025", about 0.0026", about 0.0027", about 0.0028", about 0.0029", about 0.003", about 0.0031", about 0.0032", about 0.0033", about 0.0034", about 0.0035", about 0.0036", about 0.0037", about 0.0038", about 0.0039".

In still further aspects, the thickness of the outer layer is greater at the proximal end. While in other aspects, the thickness of the outer layer is smaller at the distal end than the thickness of the outer layer at the proximal end.

In still further aspects, the outer layer can be extruded. In the aspects where the first and the second polymer layers are present, such polymer layers can be co-extruded. In still further aspects, the first polymer layer can be substantially bonded to the second polymer layer. In such exemplary aspects, the first polymer layer substantially does not delaminate from the second polymer layer. It is understood that in some aspects, the bonding can be physical or chemical, or any other type known in the art.

In yet further aspects, the outer layer is configured to apply an inward radial force on the sheath, biasing the sheath toward the unexpanded state.

In certain aspects, the first diameter (unexpanded diameter) of the lumen can be anywhere between about 10 Fr to about 16 Fr, including exemplary values of about 10.5 Fr, about 11 Fr, about 12 Fr, 12.5 Fr, about 13 Fr, about 13.5 Fr, about 14 Fr, about 14.5 Fr, about 15 Fr, and about 15.5 Fr. In yet other aspects, upon passage of the medical device the lumen can be expanded locally to the second diameter from about 20 Fr to about 26 Fr, including exemplary values of about 20.5 Fr, about 21 Fr, about 21.5 Fr, about 22 Fr, about 22.5 Fr, about 23 Fr, about 23.5 Fr, about 24 Fr, about 24.5 Fr, about 25 Fr, and about 25.5 Fr. It is understood and, as disclosed herein, the expansion (as shown in FIGS. 3A and 3B) is accomplished by sliding the first longitudinally extending edge and the second longitudinally such that the overlapping portion of the inner layer is decreased. After the passing of the device, the inner layer returns to its initial configuration having a diameter that is substantially identical to the first diameter. It is understood, and as described above, the outer layer can assist in the contraction of the inner layer by applying an inward radial force on the sheath.

Aspects of the disclosed sheath can expand to an expanded outer diameter that is from about 10% greater than the original unexpanded outer diameter to about 100% greater than the original unexpanded outer diameter, including exemplary values of about 15% greater, about 20% greater, about 25% greater, about 30% greater, about 35% greater, about 40% greater, about 45% greater, about 50% greater, about 55% greater, about 60% greater, about 65% greater, about 70% greater, about 75% greater, about 80% greater, about 85% greater, about 90% greater, and about 95% greater than the original unexpanded outer diameter.

It is understood, and as described above, the disclosed sheath can expand from its rest position. The expansion of the disclosed sheath can result in a second diameter $d_2$ that is from about 10% or less to about 430% or more than the first diameter $d_1$. In certain aspects, expansion of the sheath can result in expansion of the first diameter $d_r$ to about 10% or less, to about 9% or less, to about 8% or less, to about 7% or less, to about 6% or less, to about 5% or less, to about 4% or less, to about 3% or less, to about 2% or less, to about 1% or less. In yet other aspects, expansion of the disclosed sheath can result in expansion of the first diameter $d_r$ to about 10% or more, about 20% or more, about 30% or more, about 40% or more, about 50% or more, about 60% or more, about 70% or more, about 80% or more, about 90% or more, about 100% or more, about 125% or more, about 150% or more, about 175% or more, about 200% or more, about 225% or more, or about 250% or more.

Figure 8A:
FIGS. 8A-8C depict various portions of an exemplary sheath in various aspects.
Figure 8B:
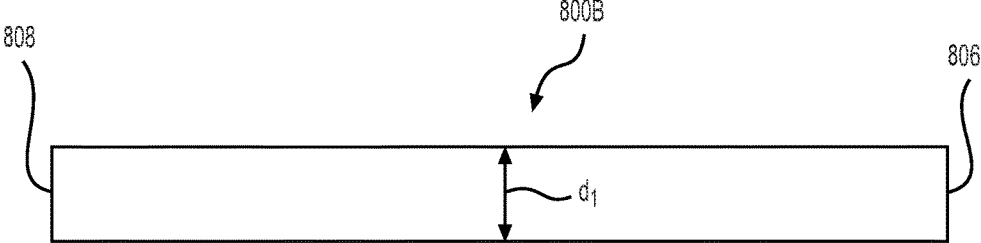
Figure 8C:
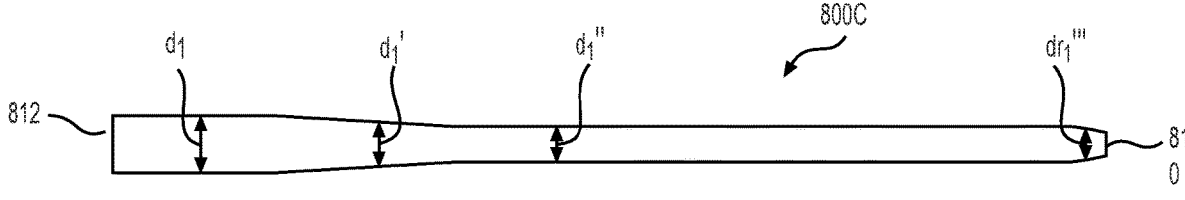

It is understood that the diameter of the sheath can be the same or different along a longitudinal axis of the sheath. The first diameter $d_1$ of the lumen 220 can vary depending on the application and size of the delivery apparatus and prosthetic device. FIG. 8A-C show various configurations and shapes of the sheath. It is understood that in some aspects, and as shown in FIG. 8B, the first diameter $d_1$ is substantially uniform along the longitudinal axis of the lumen without changing from the proximal end 808 to the distal end 806. In yet other aspects, and as shown in FIGS. 8A and 8C, the first diameter $d_1$ can vary along the longitudinal axis (for example, $d_1$ and $d_1'$ in FIG. 8A, or $d_1$, $d_1'$, $d_1''$, and $d_1'''$, as shown in FIG. 8C) of the lumen. In certain aspects, the first diameter dr1 at the proximal end 804 or 812 is larger than the first diameter $d_1'$ as shown in FIG. 8A and FIG. 8C or $d_1'''$ as shown in FIG. 8C at the distal end 802 or 810 $d_1$.

In yet further aspects, where the outer layer conforms to the shape of the inner layer, the outer diameter $d_o$ (not shown) comprises the overall diameter of the inner layer and the outer layer. In such aspects, the outer diameter $d_o$ is defined by the specific application of the sheath. Similar to the rest diameter $d_1$, the outer diameter $d_o$ of the unexpended sheath disclosed herein can be substantially uniform (constant) along the longitudinal axis of the lumen without changing from the proximal end to the distal end (not shown). In alternative aspects, the original unexpanded outer diameter $d_o$ of the disclosed sheath, similarly to the first diameter $d_1$, can decrease from the proximal end to the distal end. In some aspects, and similarly to the first diameter $d_1$, the original unexpanded outer diameter can decrease along a gradient, from the proximal end to the distal end; or it can incrementally step down along the length of the sheath having the largest original unexpanded outer diameter is near $d_o$ the proximal end, and the smallest original unexpanded outer diameter $d_o$ is near the distal end.

Different sheaths can be provided with different first diameter $d_1$, and outer diameters $d_o$, depending on the size requirements of the delivery apparatus for various applications. Additionally, some aspects can provide more or less expansion depending on the particular design parameters, the materials, and/or configurations used. In some aspects, the outer diameter $d_o$ of the sheath gradually decreases from the proximal end of the sheath to the distal end of the sheath. For example, in one aspect, the outer diameter $d_o$ can gradually decrease from about 26 Fr at the proximal end to about 18 Fr at the distal end. The diameter $d_o$ of the sheath can transition gradually across substantially the entire length of the sheath. In other aspects, the transition or reduction of the diameter of the sheath can occur only along a portion of the length of the sheath. For example, the transition can occur along a length from the proximal end to the distal end, where the length can range from about 0.5 inches to about the entire length of the sheath, including any values between any two foregoing values. In yet further aspects, the $d_o$ is minimal and constant along the section of the sheath that passes through the vasculature. In such aspects, the tapered section is about 4" or less at the proximal side of the sheath.

In still further aspects, a tie layer can be present between the outer layer and the inner layer of the sheath. In certain and unlimiting aspects, a lubricant can be applied between the overlapping portions of the encapsulated reinforcing layer to allow easier expansion during the introduction of the medical device. In such exemplary aspects, the lubricant can comprise Christo Lube supplied by ECL or MED10/6670 supplied by Nusil.

In still further aspects, the sheath, as disclosed herein, is substantially kink-resistant. Yet, in other aspects, the sheath can exhibit at least a 10% reduction, at least about 15% reduction, at least 20% reduction, at least about 25% reduction, at least about 30% reduction, at least about 35% reduction, at least about 40% reduction, at least about 45% reduction, or at least about 50% reduction in an insertion force when compared with an insertion force of in an insertion force when compared with an insertion force of a commercially available sheath or any sheath that does not comprise the disclosed herein structure.

In still further aspects, the sheath of the instant disclosure can comprise a hemostasis valve inside the lumen of the sheath, at or near the proximal end of the sheath (not shown). Additionally, the exemplary sheaths disclosed herein can comprise a soft tip at the distal end of the sheath (not shown). Such a soft tip can be provided with a lower hardness than the other portions of the sheath. In some aspects, the soft tip can have a Shore hardness from about 25 D to about 40 D, including exemplary values of about 26 D, about 27 D, about 28 D, about 29 D, about 30 D, about 31 D, about 32 D, about 33 D, about 34 D, about 35 D, about 36 D, about 37 D, about 38 D, and about 39 D. In yet other aspects, the soft tip can have a Shore hardness from about 25 A to about 40 A, including exemplary values of about 26 A, about 27 A, about 28 A, about 29 A, about 30 A, about 31 A, about 32 A, about 33 A, about 34 A, about 35 A, about 36 A, about 37 A, about 38 A, and about 39 A.

Figure 10:
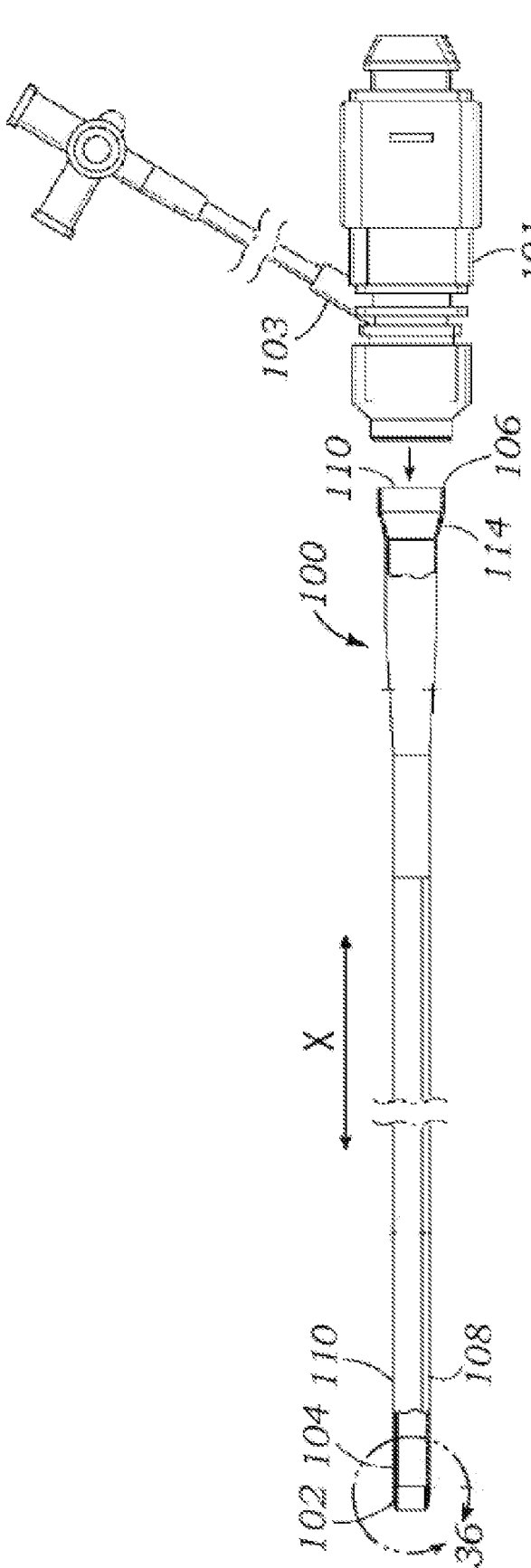
FIG. 10 depicts an exemplary delivery device.
Figure 11:
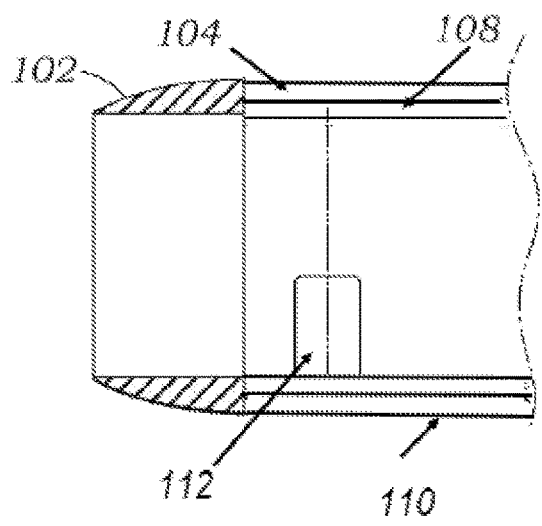
FIG. 11 depicts a portion of an exemplary sheath along line 36 of FIG. 10.

FIGS. 10 and 11 illustrate an expandable sheath 100 according to the present disclosure, which can be used with a delivery apparatus for delivering a prosthetic device, such as a tissue heart valve into a patient. In general, the delivery apparatus can include a steerable guide catheter (also referred to as a flex catheter), a balloon catheter extending through the guide catheter, and a nose catheter extending through the balloon catheter (e.g., as depicted in FIG. 1). The guide catheter, the balloon catheter, and the nose catheter can be adapted to slide longitudinally relative to each other to facilitate delivery and positioning of the valve at an implantation site in a patient's body. However, it should be noted that the sheath 100 can be used with any type of elongated delivery apparatus used for implanting balloon-expandable prosthetic valves, self-expanding prosthetic valves, and other prosthetic devices. Generally, sheath 100 can be inserted into a vessel (e.g., the femoral or iliac arteries) by passing through the skin of a patient, such that a soft tip portion 102 at the distal end 104 of the sheath 100 is inserted into the vessel. The sheath 100 can also include a proximal flared end portion 114 to facilitate mating with an introducer housing 101 (or a hub) and catheters mentioned above (e.g., the proximal flared end portion 114 can provide a compression fit over the housing tip and/or the proximal flared end portion 114 can be secured to the housing (hub) 101 via a nut or other fastening device or by bonding the proximal end of the sheath to the housing). The reinforcing layer, as described above, can comprise a plurality of extension struts 702 (FIG. 7) that allow for better mating with the hub. The introducer housing 101 can house one or more valves that form a seal around the outer surface of the delivery apparatus once inserted through the housing, as known in the art. The delivery apparatus can be inserted into and through the sheath 100, allowing the prosthetic device to be advanced through the patient's vasculature and implanted within the patient.

In exemplary aspects, the sheath 100 comprises the disclosed herein inner layer 108 and an outer layer 110 disposed around the inner layer 108. The inner layer 108 (having a reinforcing layer encapsulated into a polymer layer) defines a lumen having the first diameter $d_1$ through which a delivery apparatus can travel into a patient's vessel in order to deliver, remove, repair, and/or replace a prosthetic device, moving in a direction along the longitudinal axis X. As the prosthetic device passes through the sheath 100, the sheath locally expands from the first diameter $d_1$ to the expanded second diameter $d_2$ to accommodate the prosthetic device. After the prosthetic device passes through a particular location of the sheath 100, each successive expanded portion or segment of the sheath 100 at least partially returns to the first diameter $d_1$. In this manner, the sheath 100 can be considered self-expanding in that it does not require the use of a balloon, dilator, and/or obturator to expand.

The inner layer 108 and outer layer 110, as shown herein, can comprise any materials disclosed above.

Additionally, some aspects of a sheath 100 can include an exterior hydrophilic coating on the outer surface of the outer layer 110. Such a hydrophilic coating can facilitate insertion of the sheath 100 into a patient's vessel. Examples of suitable hydrophilic coatings include the Harmony™ Advanced Lubricity Coatings and other Advanced Hydrophilic Coatings available from SurModics, Inc., Eden Prairie, MN. DSM medical coatings (available from Koninklijke DSM N.V, Heerlen, the Netherlands), as well as other hydrophilic coatings (e.g., PTFE, polyethylene, polyvinylidene fluoride), are also suitable for use with the sheath 100.

FIG. 11 shows a portion of the exemplary sheath along line 36 in FIG. 10. In such exemplary aspects, a soft tip portion 102 can be attached to the distal end 104 of the sheath 100. Best seen in FIG. 11, the soft tip portion 102 can comprise, in some aspects, low density polyethylene (LDPE) and can be configured to minimize trauma or damage to the patient's vessels as the sheath is navigated through the vasculature. For example, in some aspects, the soft tip portion 102 can be slightly tapered to facilitate passage through the vessels. The soft tip portion 102 can be secured to the distal end 104 of the sheath 100, such as by thermally bonding the soft tip portion 102 to the inner and outer layers of the sheath 100. As disclosed above, to facilitate such mating, the reinforcing layer can comprise a plurality of reflow features 708 (FIG. 7) configured to integrally connect the distal end of the reinforcing layer with a tip of the sheath. Such a soft tip portion 102 can be provided with a lower hardness than the other portions of the sheath 100. In some aspects, the soft tip portion 102 can have a Shore hardness from about 25 A to about 40 A, including exemplary values of about 28 A, about 30 A, about 32 A, about 35 A, and about 38 A. It is further understood that Shore hardness can have any value between any two foregoing values. In yet other aspects, the soft tip portion 102 can have a Shore hardness from about 25 D to about 40 D, including exemplary values of about 28 D, about 30 D, about 32 D, about 35 D, and about 38 D. The tip portion 102 is configured to be radially expandable to allow a prosthetic device to pass through the distal opening of the sheath 100.

As shown in FIG. 11, the sheath 100 can optionally include at least one radiopaque filler or marker 112, such as a discontinuous or C-shaped band positioned near the distal end 104 of the sheath 100. The marker 112 can be associated with the inner layer 108 and/or outer layer 110 of the sheath 100. Such a radiopaque tip marker can comprise materials such as those suitable for the radiopaque filler, platinum, iridium, platinum/iridium alloys, stainless steel, other biocompatible metals, or combinations thereof. Suitable materials for use as a radiopaque filler or marker include, for example, barium sulfite, bismuth trioxide, titanium dioxide, bismuth subcarbonate, or combinations thereof. The radiopaque filler can be mixed with or embedded in the layer of the elastomeric polymer used to form the outer layer and can comprise from about 5% to about 45% by weight of the outer layer, including exemplary values of about 10%, about 15%, about 20%, about 25%, about 30%, about 35%, and about 40% by weight of the outer polymeric tubular layer. The more or less radiopaque material can be used in some aspects, depending on the particular application.

The disclosed herein sheath can be configured such that it locally expands at a particular location corresponding to the location of the medical device along the length of the lumen and then locally contracts once the medical device has passed that particular location. Thus, a bulge may be visible, traveling longitudinally along the length of the sheath as the medical device is introduced through the sheath, representing continuous local expansion and contraction as the device travels the length of the sheath. In some aspects, each segment of the sheath can locally contract after removal of any radial outward (insertion) force such that it regains the original resting (first) diameter of lumen $d_1$.

In some aspects, each segment of the sheath can locally contract after removal of any radial outward force such that it at least partially returns to the original resting (first) diameter of lumen $d_1$.

Methods

The aspects of the present disclosure also relate to a method of making a sheath comprising: rolling a reinforcing layer having an inner surface and an outer surface and a first longitudinal edge and an opposite second longitudinal edge and a width extending from the first edge to the second edge into a spiral configuration around a first mandrel having a first diameter to form a lumen having a rest diameter substantially identical to the first diameter of the mandrel, such that in the spiral configuration, at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration; removing the first mandrel; inserting a second mandrel having a second diameter larger than the first diameter into the lumen and thereby expanding the lumen to the second diameter by sliding the first edge of the reinforcing layer along at least a portion of the inner surface of the reinforcing layer and sliding the second edge of the reinforcing layer along the at least a portion of the outer surface of the reinforcing layer until the overlapping portion is substantially eliminated and a slit is formed between the first edge and the second edge of the reinforcing layer; applying a polymer layer radially outward of the reinforcing layer under conditions effective to encapsulate the reinforcing layer with the polymer layer such that the polymer layer forms a tether portion that is substantially free of the reinforcing layer and wherein the reinforcing layer and the polymer layer together form an inner layer of the sheath; and removing the inner layer from the second mandrel to allow the reinforcing layer to return to the spiral configuration having a lumen having a diameter substantially identical to the rest diameter; and positioning the inner layer on the first mandrel and applying an outer layer radially outward of the inner layer of the sheath and removing the sheath from the first mandrel.

Figure 12:
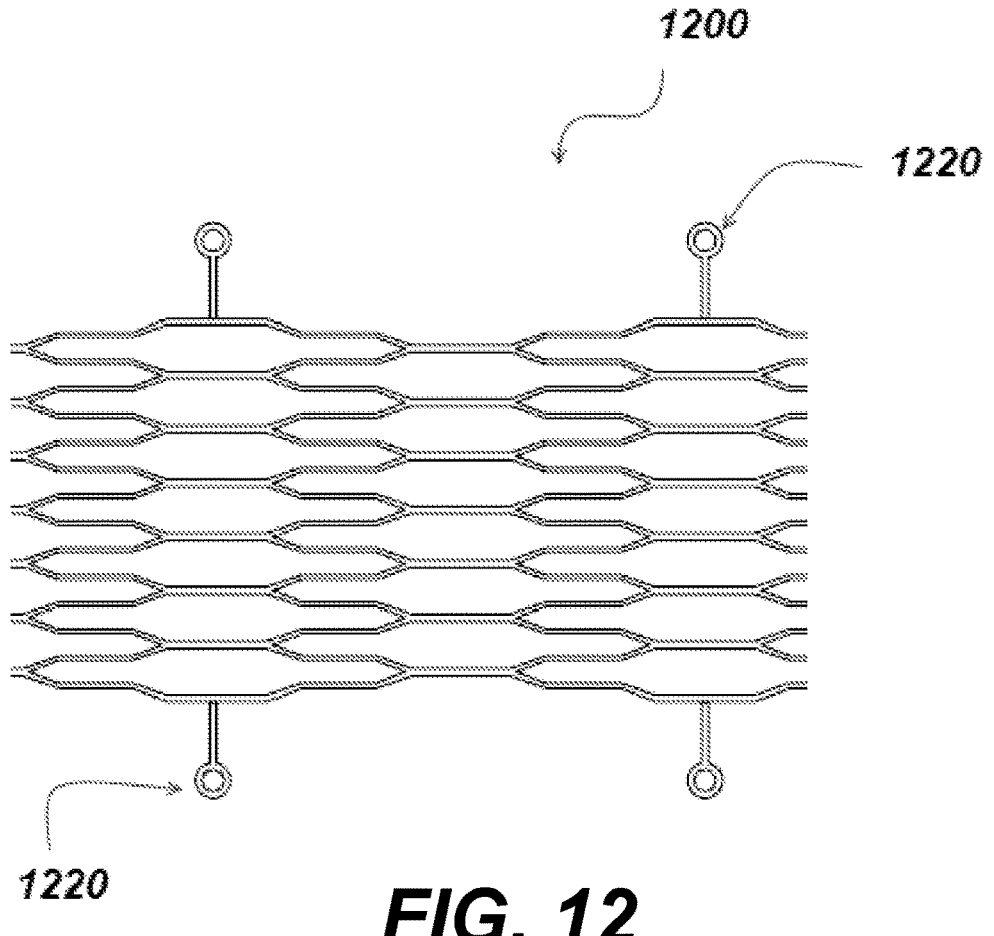
FIG. 12 depicts an exemplary planar reinforcing layer in one aspect.

Various methods can be used to produce the sheaths discussed above and below throughout the present disclosure. For example, FIG. 13 exemplifies block diagrams of one of the exemplary methods of producing the sheath in various aspects. The various methods steps are also depicted in FIGS. 12 and 14-17. In certain aspects, and as shown in FIG. 12, a planar reinforcing layer 1200 having a plurality of tabs 1220 is rolled into a spiral configuration, wherein the plurality of tabs positioned substantially perpendicular to the first edge and/or the second edge and configured to assist in the step of rolling. It is understood that these plurality of tabs are removed after the spiral configuration is formed.

Figure 13:
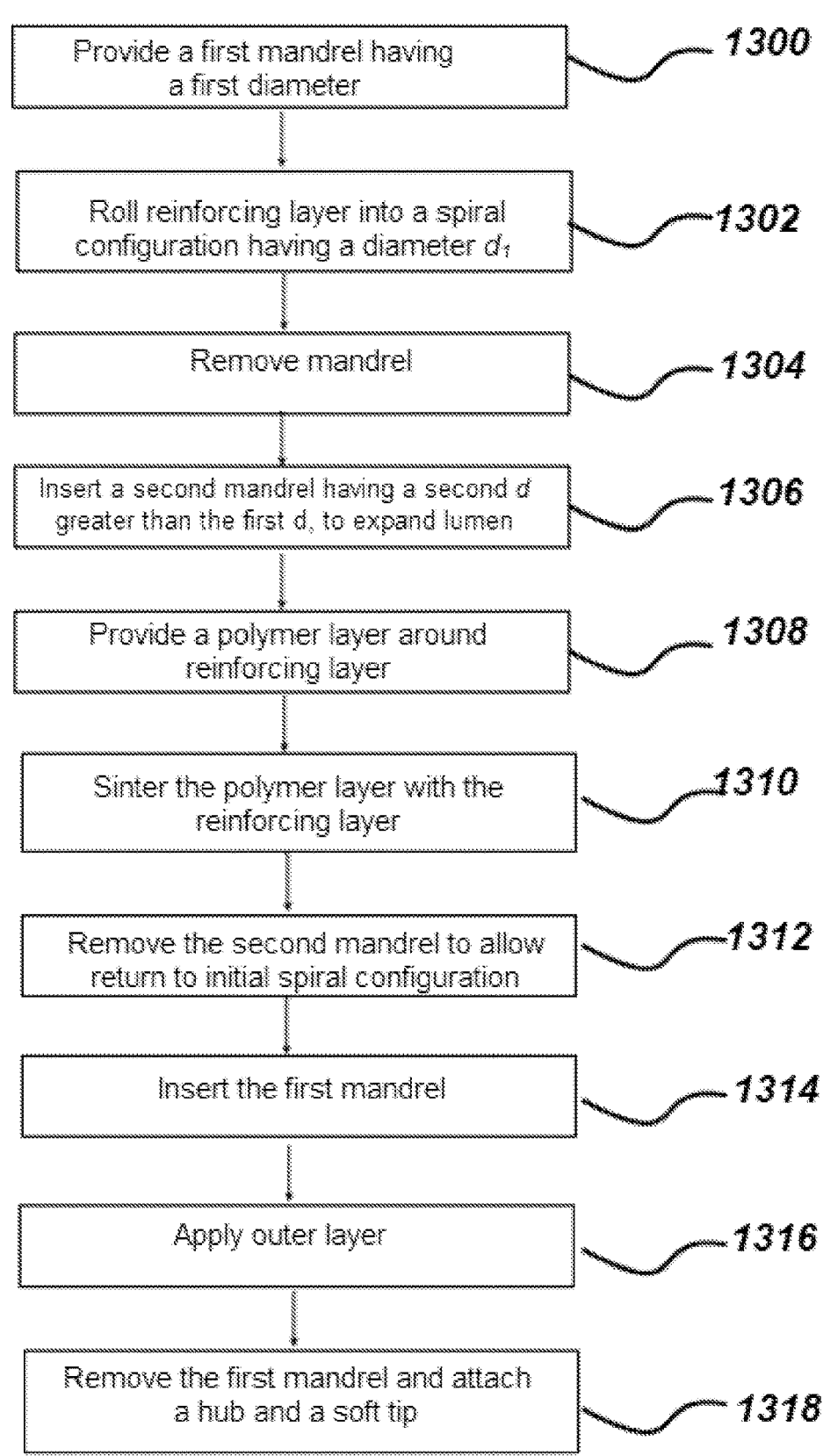
FIG. 13 depicts a block diagram of one aspect of making a sheath according to the present disclosure.
Figure 14:
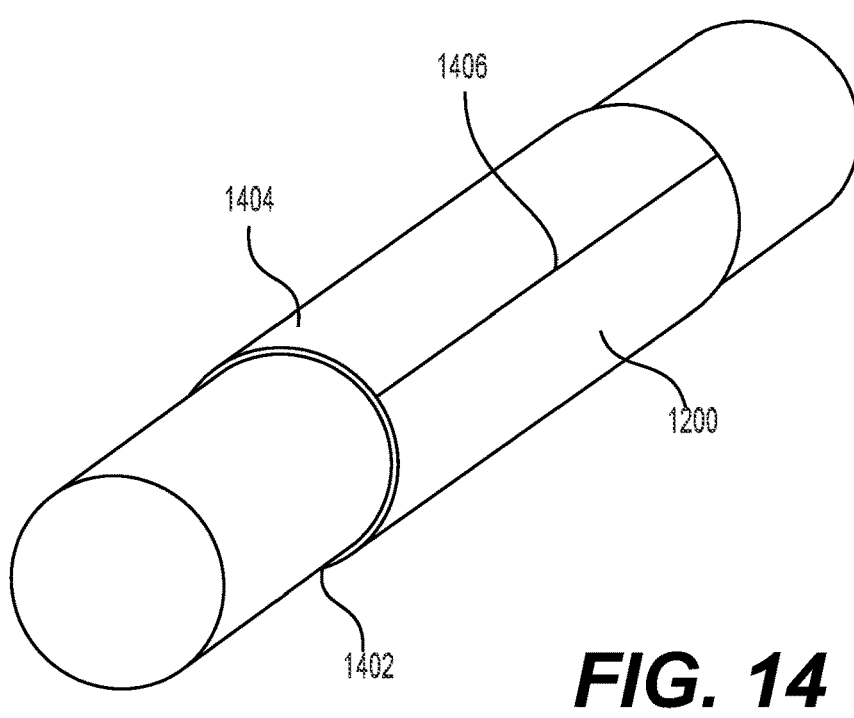
FIG. 14 depicts one aspect of a method of making a sheath according to the present disclosure.

In still further aspects, one or more mandrels can be provided (step 1300 in FIG. 13). The mandrel can be provided with an exterior coating, such as a Teflon® coating, and the mandrel's diameter can be predetermined based on the desired rest diameter $d_r$ of the resulting sheath. As shown in FIG. 14, the reinforcing layer 1200 can be rolled in a spiral configuration (step 1302, FIG. 13) around the mandrel 1402 such that in the spiral configuration, at least a portion of the inner surface of the reinforcing layer overlays at least a portion of the outer surface of the reinforcing layer to form an overlapping portion 1404 of the spiral configuration, and wherein the first longitudinal edge (not shown) is slidable along at least a portion of the inner surface of the reinforcing layer and the second longitudinal edge 1406 is slidable along at least a portion of the outer surface of the reinforcing layer to increase or decrease the overlapping portion of the spiral configuration.

In still further aspects, it is understood that the reinforcing layer rolled into the spiral configuration with the use of mandrel can have any first diameter, as described above. In certain aspects, the rest (first) diameter $d_1$ is substantially uniform along the longitudinal axis of the lumen. While in the other aspects, the rest diameter $d_1$ varies along the longitudinal axis of the lumen and wherein the rest diameter $d_1$ at the proximal end that is larger than the rest diameter $d_r$ at the distal end.

Figure 15:
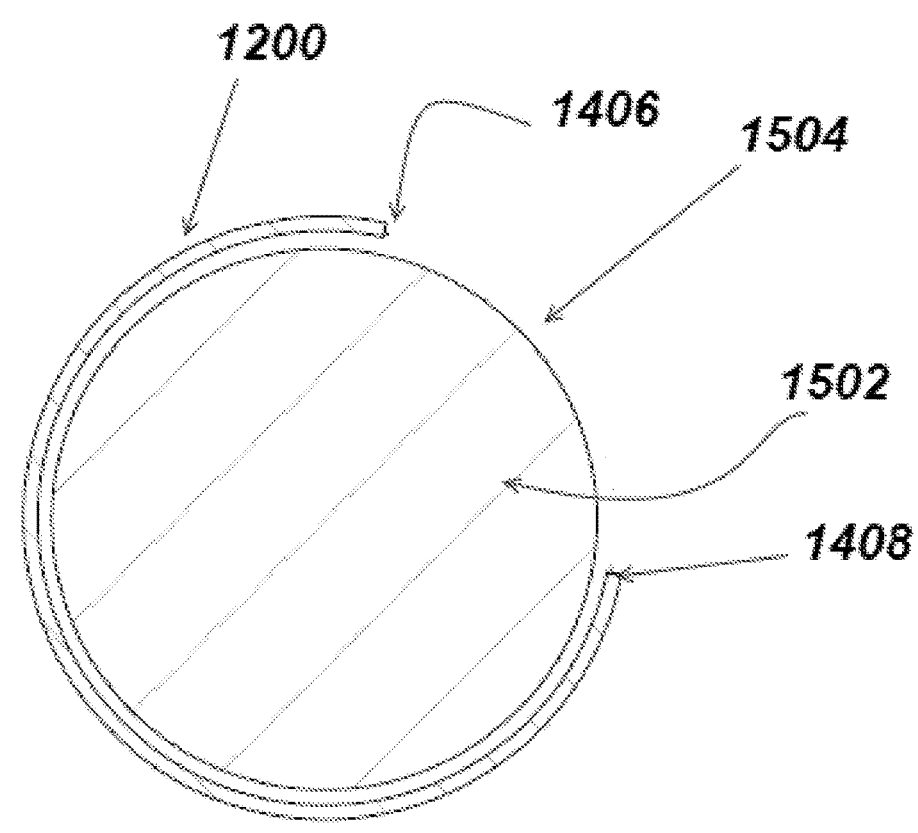
FIG. 15 depicts one aspect of a method of making a sheath according to the present disclosure.

In still further aspects, the methods can further comprise a step of removing the first mandrel (steps 1304). In still further aspects, and as shown in step 1306 of FIG. 13, a second mandrel 1502 having a second diameter that is larger than the first diameter can be inserted into the lumen. In certain aspects, a layer of the polymer layer is first disposed on the second mandrel prior to inserting it into the lumen of the spiral configuration. In further aspects, the lumen is expanded to the second diameter by sliding the first edge 1408 of the reinforcing layer 1200 along at least a portion of the inner surface of the reinforcing layer and sliding the second edge 1406 of the reinforcing layer along the at least a portion of the outer surface of the reinforcing layer until the overlapping portion is substantially eliminated and a slit 1504 is formed between the first edge and the second edge of the reinforcing layer as shown in FIG. 15.

Figure 16:
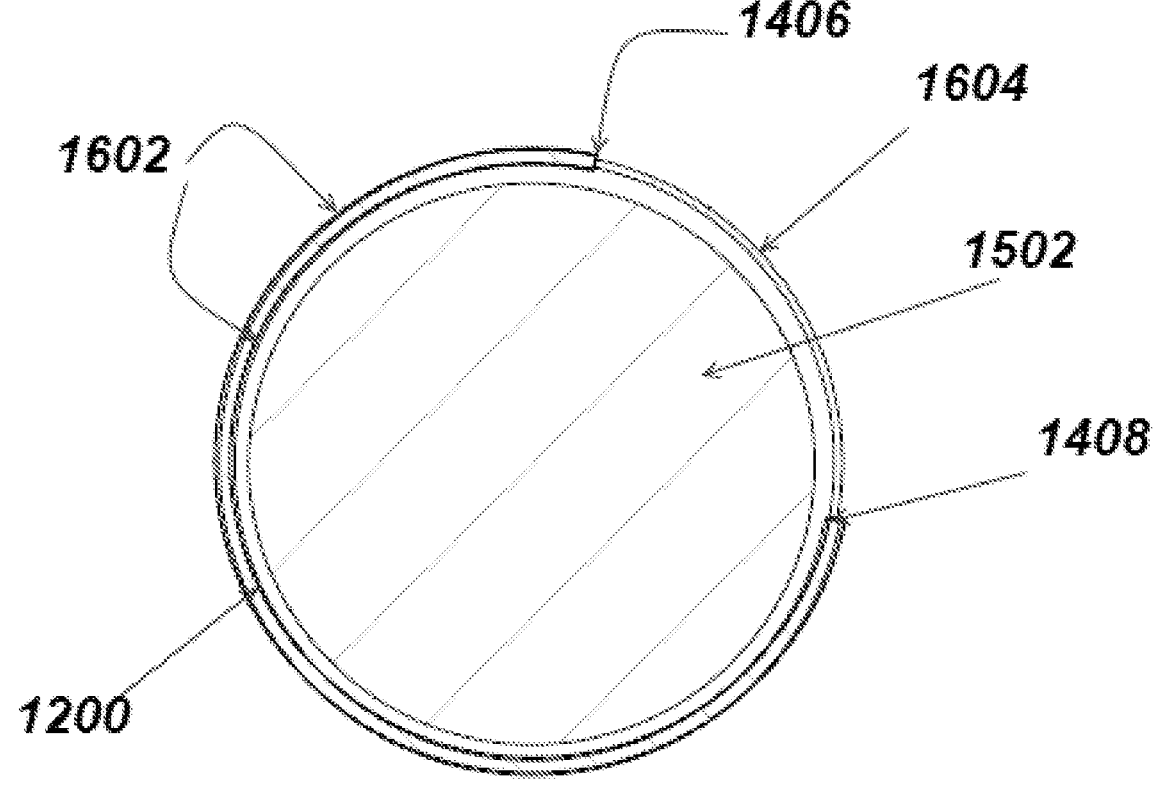
FIG. 16 depicts one aspect of a method of making a sheath according to the present disclosure.

In still further aspects, and as shown in step 1308 in FIG. 13, a polymer layer 1602 (or a second polymer layer, if the first polymer layer was initially applied) is applied radially outward of the reinforcing layer under conditions effective to encapsulate the reinforcing layer 1200 with the polymer layer 1602 such that the polymer layer forms a tether portion 1604 that is substantially free of the reinforcing layer and wherein the reinforcing layer and the polymer layer together form an inner layer of the sheath. This step can further follow by a sintering step 1310 to provide a sheath configuration as shown in FIG. 16. In aspects where two polymer layers are applied, these two polymer layers are also sintered together with the reinforcing layer.

Figure 17:
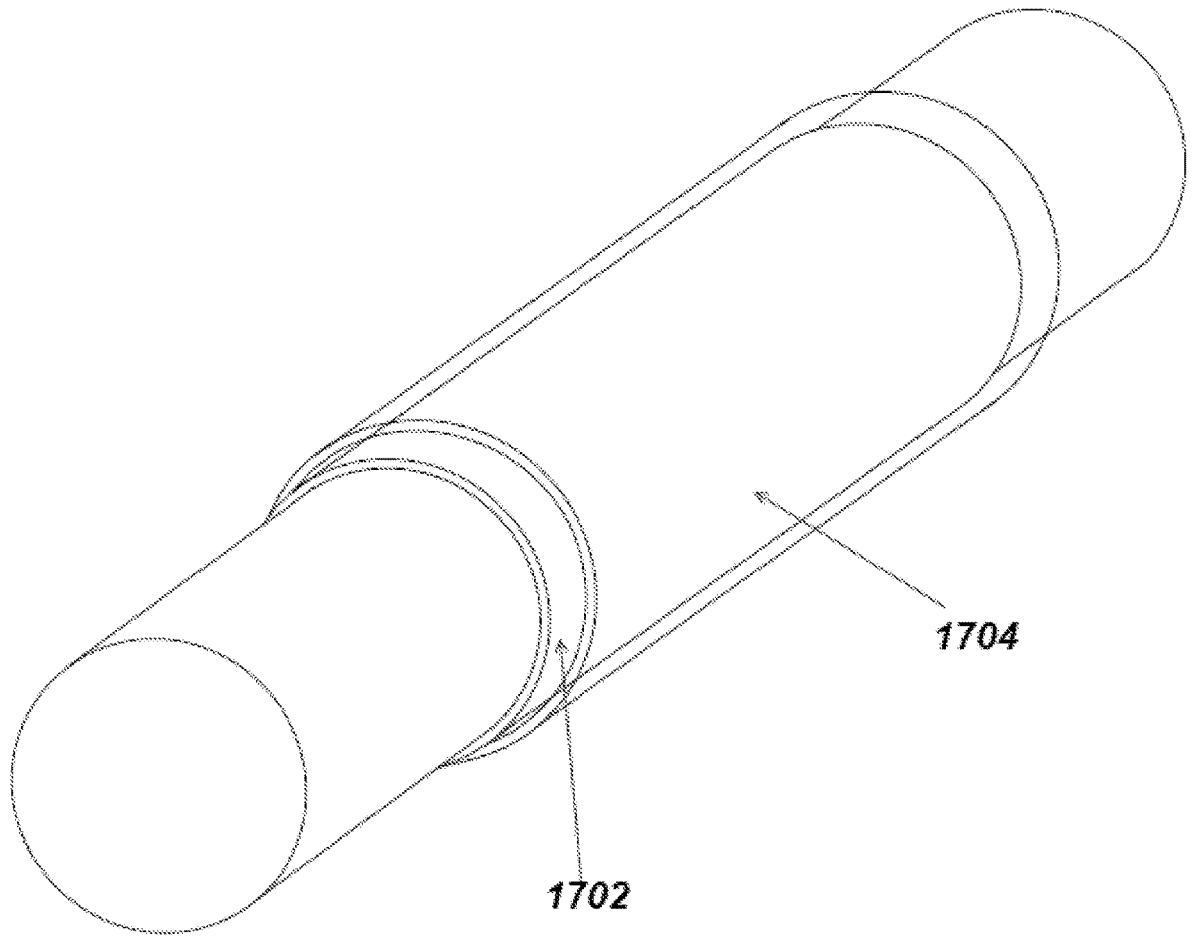
FIG. 17 depicts one aspect of a method of making a sheath according to the present disclosure

In yet further aspects and as shown in step 1312, the method can further comprise removal of the second mandrel to allow the encapsulated reinforcing layer to return to its initial spiral configuration. The spiral configuration 1702 is then positioned back on the first mandrel (step 1314) or any mandrel having the desired diameter, and an outer layer 1704 is radially applied outward of the inner layer of the sheath (step 1316) or as seen in FIG. 17. Any of the disclosed herein outer layers can be used in the disclosed herein methods.

In still further aspects, a soft, atraumatic tip can be provided at the distal end of the resulting sheath (step 1318).

In still further aspects, the disclosed herein methods can comprise a step of disposing a hydrophilic coating layer on the outer surface of the layer of the elastomeric polymer. Any disclosed herein hydrophilic coating can be used.

Sheaths of the present disclosure can be used with various methods of introducing a prosthetic device into a patient's vasculature. One such method comprises positioning an expandable sheath in a patient's vessel, passing a device through the introducer sheath, which causes a portion of the sheath surrounding the device to expand and accommodate the profile of the device, and automatically retracting the expanded portion of the sheath to its original size after the device has passed through the expanded portion. In some methods, the expandable sheath can be sutured to the patient's skin at the insertion site so that once the sheath is inserted at the proper distance within the patient's vasculature, it does not move once the implantable device starts to travel through the sheath.

Disclosed aspects of an expandable sheath can be used with other delivery and minimally invasive surgical components, such as an introducer and loader. An introducer can be inserted into the expandable sheath, and the introducer/sheath combination can be fully inserted into vasculature over a guiding device, such as a 0.35" guidewire. Once the sheath and introducer are fully inserted into a patient's vasculature, in some aspects, the expandable sheath can be sutured in place at the insertion site. In this manner, the expandable sheath can be substantially prevented from moving once positioned within the patient.

The introducer can then be removed, and the medical device, such as a transcatheter heart valve, can be inserted into the sheath, in some instances, using a loader. Such methods can additionally comprise placing the tissue heart valve in a crimped state on the distal end portion of an elongated delivery apparatus and inserting the elongated delivery device with the crimped valve into and through the expandable sheath. Next, the delivery apparatus can be advanced through the patient's vasculature to the treatment site, where the valve can be implanted.

Typically, the medical device has a greater outer diameter than the diameter of the sheath in its original configuration. The medical device can be advanced through the expandable sheath towards the implantation site, and the expandable sheath can locally expand to accommodate the medical device as the device passes through. The radial force exerted by the medical device can be sufficient to locally expand the sheath to an expanded diameter (e.g., the expanded configuration) just in the area where the medical device is currently located. Once the medical device passes a particular location of the sheath, the sheath can at least partially contract to the smaller diameter of its original configuration. The expandable sheath can thus be expanded without the use of inflatable balloons or other dilators. Once the medical device is implanted, the sheath and any sutures holding in place can be removed. In some exemplary aspects, the sheath is removed without rotating it.

In view of the many possible aspects to which the principles of the disclosed invention can be applied, it should be recognized that the illustrated aspects are only some examples of the invention and should not be taken as limiting the scope of the invention. Rather, the scope of the invention is defined by the following claims. We, therefore, claim as our invention all that comes within the scope and spirit of these claims.

EXEMPLARY ASPECTS

Example 1

A sheath for delivering a medical device, wherein the sheath has a proximal end and a distal end and comprises: a) an inner layer comprising: i) a reinforcing layer having an inner surface and an outer surface and a first longitudinal edge and an opposite second longitudinal edge, and wherein the reinforcing layer has a width extending from the first edge to the second edge; ii) a polymer layer; and b) an outer layer; wherein the reinforcing layer is rolled longitudinally into a spiral configuration such that at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration, wherein the polymer layer extends circumferentially around the reinforcing layer such that the reinforcing layer is substantially encapsulated within the polymer layer; wherein the polymer layer comprises a tether portion that is substantially free of the reinforcing layer; wherein the polymer layer forms a substantially circular enclosed shape of the inner layer; wherein the inner layer forms a lumen configured to receive the medical device; wherein the sheath is in an unexpanded state, the lumen has a first diameter; and wherein the lumen is configured to expand to a second diameter by sliding the first edge of the reinforcing layer along at least a portion of the inner surface of the reinforcing layer and sliding the second edge of the reinforcing layer along the at least a portion of the outer surface of the reinforcing layer, during application of a radial outward force by passage of the medical device through the lumen.

Example 2

The sheath of any examples herein, particularly example 1, wherein in the unexpanded state, the overlapping portion comprises about 30-70% of the reinforcing layer width.

Example 3

The sheath of any examples herein, particularly examples 1 or 2, wherein in an expanded state, the overlapping portion comprises about 10-20% of the reinforcing layer width.

Example 4

The sheath of any examples herein, particularly examples 1-3, wherein the tether portion of the polymer layer comprises a first portion of the polymer layer extending beyond the first edge of the reinforcing layer, a second portion of the polymer layer extending beyond the second edge of the reinforcing layer, and a third portion that continuously extends between the first portion and the second portion.

Example 5

The sheath of any examples herein, particularly example 4, wherein the first portion, the second portion, and the third portion of the tether portion of the polymer layer form at least one fold that at least partially positioned within the overlapping portion of the spiral configuration.

Example 6

The sheath of any examples herein, particularly examples 1-5, wherein the reinforcing layer comprises a polymer or a metal.

Example 7

The sheath of any examples herein, particularly example 6, wherein the polymer comprises PEEK, nylon, or a combination thereof.

Example 8

The sheath of any examples herein, particularly examples 6 or 7, wherein the polymer exhibits a modulus between about 1 GPa to about 10 GPa.

Example 9

The sheath of any examples herein, particularly example 6, wherein the reinforcing layer comprises a metal.

Example 10

The sheath of any examples herein, particularly example 9, wherein the reinforcing layer is a metallic etched sheet.

Example 11

The sheath of any examples herein, particularly example 9, wherein the reinforcing layer is a metallic laser-cut sheet.

Example 12

The sheath of any examples herein, particularly example 9, wherein the reinforcing layer is a metallic laser-cut tube.

Example 13

The sheath of any examples herein, particularly example 12, wherein the tube is a hypotube.

Example 14

The sheath of any examples herein, particularly examples 1-13, wherein the reinforcing layer comprises a cut, or an etch pattern having a regular or irregular shape.

Example 15

The sheath of any examples herein, particularly example 14, wherein the cut or the etch pattern is repetitive.

Example 16

The sheath of any examples herein, particularly examples 14 or 15, wherein the cut pattern comprises a c-cut, a diamond-cut, a spiral-cut, an interrupted cut, or any combination thereof.

Example 17

The sheath of any examples herein, particularly example 14-16, wherein a cut or an etch pitch, and a cut or an etch density of the cut, or the etch pattern vary along a length of the reinforcing layer to incorporate various stiffness profiles.

Example 18

The sheath of any examples herein, particularly examples 9-17, wherein the reinforcing layer comprises a metal having a modulus from about 20 GPa to about 250 GPa to achieve a predetermined stiffness profile.

Example 19

The sheath of any examples herein, particularly examples 14-18, wherein the reinforcing layer comprises a plurality of enclosed interstices formed by the cut or the etch pattern.

Example 20

The sheath of any examples herein, particularly example 19, wherein the plurality of enclosed interstices are filled with at least a portion of the polymer layer.

Example 21

The sheath of any examples herein, particularly examples 14-20, wherein the reinforcing layer comprises a repetitive cut or etch pattern arranged in a plurality of rows, wherein each row comprises a plurality of struts forming a first plurality of enclosed interstices, wherein each of the plurality of enclosed interstices has a central portion, an enclosed first end portion and an enclosed second end portion, wherein the central portion of the interstice has a first width, the first end portion of the interstice has a second width, and the second end portion of the interstice has a third width.

Example 22

The sheath of any examples herein, particularly example 21, wherein the second width is substantially identical to the third width.

Example 23

The sheath of any examples herein, particularly examples 21 or 22, wherein the first width is greater than the second width and the third width.

Example 24

The sheath of any examples herein, particularly examples 21-23, wherein the central portion comprises a first strut and an opposite second strut, and wherein two abut interstices share at least a portion of the first strut or the second strut.

Example 25

The sheath of any examples herein, particularly example 24, wherein each of the first and the second strut has a first end and a second end and a straight portion extending between the first end and the second end; wherein each of the first and the second struts split at the first end into a first arm and a second arm in a first slingshot configuration and at the second end into a third arm and a fourth arm in a second slingshot configuration; wherein the second arm of the first strut and the first arm of the second strut gather to form an enclosed first end portion; and wherein the fourth arm of the first strut and the third arm of the second strut gather to form the enclosed second portion.

Example 26

The sheath of any examples herein, particularly example 25, wherein at a gathering point, the second arm of the first strut and the first arm of the second strut extend into a first bridging member in a slingshot configuration connecting between the first end portion of the interstice in one row and a second end portion of the interstice in a row below.

Example 27

The sheath of any examples herein, particularly examples 25-26, wherein at a gathering point the fourth arm of the first strut and the third arm of the second strut extend into a second bridging member connecting the second end portion of the interstice in one row and a first end portion of the interstice in a row above.

Example 28

The sheath of any examples herein, particularly example 27, wherein two of the first bridging members of each of two abut interstices form a second plurality of enclosed interstices between one row and the row below.

Example 29

The sheath of any examples herein, particularly examples 27-28, wherein two of the second bridging members of each of two abut interstices form a third plurality of enclosed interstices between one row and the row above.

Example 30

The sheath of any examples herein, particularly examples 21-29, wherein an enclosed interstice in each of the plurality of rows positioned along the first edge or the second edge of the reinforcing member comprises a central portion comprising at least one strut that does not split into arms.

Example 31

The sheath of any examples herein, particularly examples 21-30, wherein the straight portion of the first and the second struts have a thickness greater than a thickness of the first, second, third, or fourth arms.

Example 32

The sheath of any examples herein, particularly examples 14-20, wherein the reinforcing layer comprises a plurality of longitudinally undulating struts, wherein the undulating struts form a plurality of consecutive valleys and apexes, and wherein two longitudinally adjacent struts have an opposite undulation phase such that each of the plurality of valleys of a first strut is proximal to each of the apexes of a first adjacent strut, and wherein each of the apexes of the first strut is proximal to each of the plurality of valleys of a second adjacent strut.

Example 33

The sheath of any examples herein, particularly example 32, wherein a first bridge member extends from at least a portion of the each of the plurality of valleys of the first strut to at least a portion of the each of the apexes of the first adjacent strut and wherein a second bridge member extends from at least a portion of the each of the apexes of the first strut to at least a portion of the each of the plurality of valleys of the second adjacent strut, thereby forming rows of enclosed interstices between every two adjacent struts.

Example 34

The sheath of any examples herein, particularly examples 1-33, wherein a distal end of the reinforcing layer is different from a proximal end of the reinforcing layer.

Example 35

The sheath of any examples herein, particularly example 34, wherein the proximal end of the reinforcing layer comprises a plurality of extension struts configured to secure the reinforcing layer to a hub.

Example 36

The sheath of any examples herein, particularly example 35, wherein the plurality of extension struts is flared out radially.

Example 37

The sheath of any examples herein, particularly examples 35 or 36, wherein the plurality of extension struts have a T-bar shape.

Example 38

The sheath of any examples herein, particularly examples 35 or 36, wherein the plurality of extension struts have an island shape.

Example 39

The sheath of any examples herein, particularly examples 34-38, wherein the distal end of the reinforcing layer comprises an enclosed distal end portion connecting all enclosed interstices present proximally to the enclosed distal end portion.

Example 40

The sheath of any examples herein, particularly example 39, wherein the enclosed distal end portion comprises a plurality of reflow features configured to integrally connect the distal end of the reinforcing layer with a tip of the sheath.

Example 41

The sheath of any examples herein, particularly examples 1-40, wherein the reinforcing member has a thickness from about 0.001" to about 0.020".

Example 42

The sheath of any examples herein, particularly examples 1-41, wherein the reinforcing member comprises titanium metal, nitinol, stainless steel, cobalt-chromium alloy, or any combination or alloys thereof.

Example 43

The sheath of any examples herein, particularly examples 1-42, wherein the polymer layer is lubricious.

Example 44

The sheath of any examples herein, particularly examples 1-43, wherein the polymer layer is substantially not stretchable.

Example 45

The sheath of any examples herein, particularly examples 1-44, wherein the polymer layer comprises e-PTFE.

Example 46

The sheath of any examples herein, particularly example 45, wherein the polymer layer is sintered with the reinforcing layer.

Example 47

The sheath of any examples herein, particularly examples 1-46, wherein a combined thickness of the polymer layer and the reinforcing layer is from about 0.003" to about 0.030".

Example 48

The sheath of any examples herein, particularly examples 21-47, wherein a thickness of the polymer layer within the plurality of enclosed interstices is from less than about 0.001" to about 0.010".

Example 49

The sheath of any examples herein, particularly examples 1-48, wherein the outer layer comprises an elastomeric material.

Example 50

The sheath of any examples herein, particularly examples 1-49, wherein the outer layer comprises a compound comprising a heat shrinking material, a polyether block amide, a polyurethane, silicone, polyisoprene, or any combination thereof present up to 100 wt % based on a total weight of the compound.

Example 51

The sheath of any examples herein, particularly example 50, wherein the outer layer comprises PEBAX®.

Example 52

The sheath of any examples herein, particularly examples 1-51, wherein the outer layer has a thickness from about 0.003" to about 0.010".

Example 53

The sheath of any examples herein, particularly examples 1-52, wherein the outer layer has a Shore hardness of from about 25 Durometer to about 90 Durometer.

Example 54

The sheath of any examples herein, particularly examples 50-53, wherein the compound further comprises an inorganic filler present in an amount of less than about 60 wt % based on the total weight of the compound.

Example 55

The sheath of any examples herein, particularly examples 50-54, wherein the compound further comprises a solid lubricant present up to about 20 wt % based on the total weight of the compound.

Example 56

The sheath of any examples herein, particularly examples 1-55, wherein the outer layer comprises one or more sublayers.

Example 57

The sheath of any examples herein, particularly example 56, wherein each of the sublayers are the same or different.

Example 58

The sheath of any examples herein, particularly examples 1-57, wherein the outer layer is configured to apply an inward radial force on the sheath, biasing the sheath toward the unexpanded state.

Example 59

The sheath of any examples herein, particularly examples 1-58, wherein a tie layer is disposed between the inner layer and the outer layer of the sheath.

Example 60

The sheath of any examples herein, particularly examples 1-59, wherein the sheath is substantially kink-resistant.

Example 61

A method of making a sheath for delivering a medical device comprising: rolling a reinforcing layer having an inner surface and an outer surface and a first longitudinal edge and an opposite second longitudinal edge, and a width extending from the first edge to the second edge into a spiral configuration around a first mandrel having a first diameter to form a lumen having a rest diameter substantially identical to the first diameter of the mandrel; such that in the spiral configuration, at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration; removing the first mandrel; inserting a second mandrel having a second diameter larger than the first diameter into the lumen and thereby expanding the lumen to the second diameter by sliding the first edge of the reinforcing layer along at least a portion of the inner surface of the reinforcing layer and sliding the second edge of the reinforcing layer along the at least a portion of the outer surface of the reinforcing layer until the overlapping portion is substantially eliminated and a slit is formed between the first edge and the second edge of the reinforcing layer; applying a polymer layer radially outward of the reinforcing layer under conditions effective to encapsulate the reinforcing layer with the polymer layer such that the polymer layer forms a tether portion that is substantially free of the reinforcing layer and wherein the reinforcing layer and the polymer layer together form an inner layer of the sheath; and removing the inner layer from the second mandrel to allow the reinforcing layer to return to the spiral configuration having a lumen having a diameter substantially identical to the rest diameter; positioning the inner layer on the first mandrel and applying an outer layer radially outward of the inner layer of the sheath and removing the sheath from the first mandrel.

Example 62

The method of any examples herein, particularly example 61, wherein the first edge and/or the second edge of the reinforcing layer comprises a plurality of tabs positioned substantially perpendicular to the first edge and/or the second edge and configured to assist in the step of rolling.

Example 63

The method of any examples herein, particularly example 62, wherein the plurality of tabs are removed after the spiral configuration is formed.

Example 64

The method of any examples herein, particularly example 62 or 63, wherein the tether portion of the polymer layer comprises a first portion of the polymer layer extending beyond the first edge of the reinforcing layer, a second portion of the polymer layer extending beyond the second edge of the reinforcing layer, and a third portion that continuously extends between the first portion and the second portion.

Example 65

The method of any examples herein, particularly example 64, wherein the first portion, the second portion, and the third portion of the tether portion of the polymer layer form a fold that is at least partially positioned within the overlapping portion of the spiral configuration.

Example 66

The method of any examples herein, particularly examples 61-65, wherein the conditions effective to encapsulate the reinforcing layer with the polymer layer comprise a sintering step.

Example 67

The method of any examples herein, particularly examples 61-66, the overlapping portion of the spiral configuration having the lumen having the rest diameter, comprises about 30-70% of the reinforcing layer width.

Example 68

The method of any examples herein, particularly examples 61-67, wherein the lumen is configured to expand to an expanded diameter upon passage of the medical device through the lumen by decreasing the overlapping portion of the spiral configuration.

Example 69

The method of any examples herein, particularly example 68, wherein the overlapping portion comprises about 10-20% of the reinforcing layer width.

Example 70

The method of any examples herein, particularly examples 61-69, wherein the reinforcing layer comprises a polymer or a metal.

Example 71

The method of any examples herein, particularly example 70, wherein the polymer comprises PEEK, nylon, or a combination thereof.

Example 72

The method of any examples herein, particularly example 70 or 71, wherein the polymer exhibits a modulus between about 1 GPa to about 10 GPa.

Example 73

The sheath of any examples herein, particularly example 70, wherein the reinforcing layer comprises a metal.

Example 74

The method of any examples herein, particularly example 73, wherein the reinforcing layer is a metallic etched sheet.

Example 75

The method of any examples herein, particularly example 73, wherein the reinforcing layer is a metallic laser-cut sheet.

Example 76

The method of any examples herein, particularly example 73, wherein the reinforcing layer is a metallic laser-cut tube.

Example 77

The method of any examples herein, particularly example 76, wherein the tube is a hypotube.

Example 78

The method of any examples herein, particularly examples 61-77, wherein the reinforcing layer comprises a cut, or an etch pattern having a regular or irregular shape.

Example 79

The method of any examples herein, particularly example 78, wherein the cut or the etch pattern is repetitive.

Example 80

The method of any examples herein, particularly example 78 or 79, wherein the cut pattern comprises a c-cut, a-diamond cut, a spiral-cut, an interrupted cut, or any combination thereof.

Example 81

The method of any examples herein, particularly examples 78-80, wherein a cut or an etch pitch and a cut, or an etch density of the cut, or the etch pattern vary along a length of the reinforcing layer to incorporate various stiffness profiles.

Example 82

The method of any examples herein, particularly examples 73-81, wherein the reinforcing layer comprises a metal having a modulus from about 20 GPa to about 250 GPa to achieve a predetermined stiffness profile.

Example 83

The method of any examples herein, particularly examples 78-82, wherein the reinforcing layer comprises a plurality of enclosed interstices formed by the cut or the etch pattern.

Example 84

The method of any examples herein, particularly example 83, wherein the plurality of enclosed interstices are filled with at least a portion of the polymer layer.

Example 85

The method of any examples herein, particularly examples 78-84, wherein the reinforcing layer comprises a repetitive cut or etch pattern arranged in a plurality of rows, wherein each row comprises a plurality of struts forming a first plurality of enclosed interstices, wherein each of the plurality of enclosed interstices has a central portion, an enclosed first end portion and an enclosed second end portion, wherein the central portion of the interstice has a first width, the first end portion of the interstice has a second width, and the second end portion of the interstice has a third width.

Example 86

The method of any examples herein, particularly example 85, wherein the second width is substantially identical to the third width.

Example 87

The method of any examples herein, particularly example 85 or 86, wherein the first width is greater than the second width and the third width.

Example 88

The method of any examples herein, particularly examples 85-87, wherein the central portion comprises a first strut and an opposite second strut, and wherein two abut interstices share at least a portion of the first strut or the second strut.

Example 89

The method of any examples herein, particularly example 88, wherein each of the first and the second strut has a first end and a second end and a straight portion extending between the first end and the second end; wherein each of the first and the second struts split at the first end into a first arm and a second arm in a first slingshot configuration and at the second end into a third arm and a fourth arm in a second slingshot configuration; wherein the second arm of the first strut and the first arm of the second strut gather to form the enclosed first end portion; and wherein the fourth arm of the first strut and the third arm of the second strut gather to form the enclosed second end portion.

Example 90

The method of any examples herein, particularly example 89, wherein at a gathering point, the second arm of the first strut and the first arm of the second strut extend into a first bridging member in a slingshot configuration connecting between the first end portion of the interstice in one row and a second end portion of the interstice in a row below.

Example 91

The method of any examples herein, particularly examples 89-90, wherein at a gathering point the fourth arm of the first strut and the third arm of the second strut extend into a second bridging member connecting the second end portion of the interstice in one row and a first end portion of the interstice in a row above.

Example 92

The method of any examples herein, particularly example 91, wherein two of the first bridging members of each of two abut interstices form a second plurality of enclosed interstices between one row and the row below.

Example 93

The method of any examples herein, particularly examples 90-91, wherein two of the second bridging members of each of two abut interstices form a third plurality of enclosed interstices between one row and the row above.

Example 94

The method of any examples herein, particularly examples 84-93, wherein an enclosed interstice in each of the plurality of rows positioned along the first edge or the second edge of the reinforcing member comprises a central portion comprising at least one strut that does not split into arms.

Example 95

The method of any examples herein, particularly examples 84-93, wherein the straight portion of the first and the second struts have a thickness greater than a thickness of the first, second, third, or fourth arms.

Example 96

The method of any examples herein, particularly examples 78-84, wherein the reinforcing layer comprises a plurality of longitudinally undulating struts, wherein the undulating struts form a plurality of consecutive valleys and apexes, and wherein two longitudinally adjacent struts have an opposite undulation phase such that each of the plurality of valleys of a first strut is proximal to each of the apexes of a first adjacent strut, and wherein each of the apexes of the first strut is proximal to each of the plurality of valleys of a second adjacent strut.

Example 97

The method of any examples herein, particularly example 96, wherein a first bridge member extends from at least a portion of the each of the plurality of valleys of the first strut to at least a portion of the each of the apexes of the first adjacent strut and wherein a second bridge member extends from at least a portion of the each of the apexes of the first strut to at least a portion of the each of the plurality of valleys of the second adjacent strut, thereby forming rows of enclosed interstices between every two adjacent struts.

Example 98

The method of any examples herein, particularly examples 61-97, wherein a distal end of the reinforcing layer is different from a proximal end of the reinforcing layer.

Example 99

The method of any examples herein, particularly example 98, wherein the proximal end of the reinforcing layer comprises a plurality of extension struts configured to secure the reinforcing layer to a hub.

Example 100

The method of any examples herein, particularly example 99, wherein the plurality of extension struts is flared out radially.

Example 101

The method of any examples herein, particularly example 99 or 100, wherein the plurality of extension struts have a T-bar shape.

Example 102

The method of any examples herein, particularly example 99 or 100, wherein the plurality of extension struts have an island shape.

Example 103

The method of any examples herein, particularly examples 99-102, wherein the distal end of the reinforcing layer comprises an enclosed distal end portion connecting all enclosed interstices present proximally to the enclosed distal end portion.

Example 104

The method of any examples herein, particularly example 103, wherein the enclosed distal end portion comprises a plurality of reflow features configured to integrally connect the distal end of the reinforcing layer with a tip of the sheath.

Example 105

The method of any examples herein, particularly examples 61-104, wherein the reinforcing member has a thickness from about 0.001 inches to about 0.020 inches.

Example 106

The method of any examples herein, particularly examples 61-105, wherein the reinforcing member comprises titanium metal, nitinol, stainless steel, cobalt-chromium alloy, or any combination or alloys thereof.

Example 107

The method of any examples herein, particularly examples 61-106, wherein the polymer layer is lubricious.

Example 108

The method of any examples herein, particularly examples 61-107, wherein the polymer layer is substantially not stretchable.

Example 109

The method of any examples herein, particularly examples 61-108, wherein the polymer layer comprises e-PTFE.

Example 110

The method of any examples herein, particularly examples 61-109, wherein a combined thickness of the polymer layer and the reinforcing layer is from about 0.003" to about 0.030".

Example 111

The method of any examples herein, particularly examples 84-110, wherein a thickness of the polymer layer within the plurality of enclosed interstices is from about less than about 0.001" to about 0.010".

Example 112

The method of any examples herein, particularly examples 61-111, wherein the outer layer comprises an elastomeric material.

Example 113

The method of any examples herein, particularly examples 61-112, wherein the outer layer comprises a compound comprising a heat shrinking material, a polyether block amide, a polyurethane, silicone, polyisoprene, or any combination thereof present up to 100 wt % based on a total weight of the compound.

Example 114

The method of any examples herein, particularly example 113, wherein the outer layer comprises PEBAX®.

Example 115

The method of any examples herein, particularly examples 61-114, wherein the outer layer has a thickness from about 0.003" to about 0.010".

Example 116

The method of any examples herein, particularly examples 61-115, wherein the outer layer has a Shore hardness of from about 25 Durometer to about 75 Durometer.

Example 117

The method of any examples herein, particularly examples 111-116, wherein the compound further comprises an inorganic filler present in an amount of less than about 60 wt % based on the total weight of the compound.

Example 118

The method of any examples herein, particularly examples 111-117, wherein the compound further comprises a solid lubricant present up to about 20 wt % based on the total weight of the compound.

Example 119

The method of any examples herein, particularly examples 61-118, wherein the outer layer comprises one or more sublayers.

Example 120

The method of any examples herein, particularly example 119, wherein each of the sublayers is the same or different.

Example 121

The method of any examples herein, particularly examples 61-120, wherein the outer layer is configured to apply an inward radial force on the sheath, biasing the sheath toward the unexpanded state.

Example 122

The method of any examples herein, particularly examples 61-121, wherein a tie layer is disposed between the inner layer and the outer layer of the sheath.

Example 123

The method of any examples herein, particularly examples 61-122, wherein the sheath is substantially kink-resistant.

Example 124

A method of delivering a medical device through a sheath, the method comprising: a) introducing the medical device into a proximal end of a lumen having a first diameter and wherein the lumen is formed by an inner layer, wherein the inner layer comprises: i) a reinforcing layer having an inner surface and an outer surface and a first longitudinal edge and an opposite second longitudinal edge, and wherein the reinforcing layer has a width extending from the first edge to the second edge; and ii) a polymer layer; wherein the reinforcing layer is rolled longitudinally into a spiral configuration such that at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration, wherein the polymer layer extends circumferentially around the reinforcing layer such that the reinforcing layer is substantially encapsulated within the polymer layer; wherein the polymer layer comprises a tether portion that is substantially free of the reinforcing layer; and wherein the polymer layer forms a substantially circular enclosed shape of the inner layer; b) advancing the medical device through the lumen such that the medical device exerts a radially outward force on the inner layer, such that the lumen expands to a second diameter by sliding the first edge of the reinforcing layer along at least a portion of the inner surface of the reinforcing layer and sliding the second edge of the reinforcing layer along the at least a portion of the outer surface of the reinforcing layer;

and c) locally contracting the expanded sheath back to an unexpanded configuration by radially compressing the expanded portion with a radially inward bias of an outer layer that extends around the inner layer.

Example 125

The method of any examples herein, particularly example 124, wherein the medical device is a prosthetic heart valve mounted in a radially crimped state on a delivery apparatus, and the act of advancing the medical device through the sheath comprises advancing the delivery apparatus and the prosthetic heart valve into the vasculature of a patient.

The invention claimed is:

1. A sheath for delivering a medical device, wherein the sheath has a proximal end and a distal end and comprises:
   an inner layer comprising:
      a reinforcing layer having an inner surface and an outer surface and a first longitudinal edge and an opposite second longitudinal edge, and wherein the reinforcing layer has a width extending from the first edge to the second edge;
      a polymer layer; and
   an outer layer;
   wherein the reinforcing layer is rolled longitudinally into a spiral configuration such that at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration,
   wherein the polymer layer extends circumferentially around the reinforcing layer such that the reinforcing layer is substantially encapsulated within the polymer layer;
   wherein the polymer layer comprises a tether portion that is substantially free of the reinforcing layer;
   wherein the polymer layer forms a substantially circular enclosed shape of the inner layer;
   wherein the inner layer forms a lumen configured to receive the medical device;
   wherein the sheath is in an unexpanded state, the lumen has a first diameter; and
   wherein the lumen is configured to expand to a second diameter by sliding the first edge of the reinforcing layer along at least a portion of the inner surface of the reinforcing layer and sliding the second edge of the reinforcing layer along the at least a portion of the outer surface of the reinforcing layer, during application of a radial outward force by passage of the medical device through the lumen.

2. The sheath of claim 1, wherein in the unexpanded state, the overlapping portion comprises about 30-70% of the reinforcing layer width,
   wherein in an expanded state, the overlapping portion comprises about 10-20% of the reinforcing layer width.

3. The sheath of claim 1, wherein the tether portion of the polymer layer comprises a first portion of the polymer layer extending beyond the first edge of the reinforcing layer, a second portion of the polymer layer extending beyond the second edge of the reinforcing layer, and a third portion that continuously extends between the first portion and the second portion.

4. The sheath of claim 3, wherein the first portion, the second portion, and the third portion of the tether portion of the polymer layer form at least one fold that is at least partially positioned within the overlapping portion of the spiral configuration.

5. The sheath of claim 1, wherein the reinforcing layer is a metallic etched sheet, or a metallic laser-cut sheet, or a metallic laser-cut tube, or a combination thereof.

6. The sheath of claim 1, wherein the reinforcing layer comprises a cut, or an etch pattern having a regular or irregular shape, wherein the cut or the etch pattern form a plurality of enclosed interstices, where the plurality of enclosed interstices are filled with at least a portion of the polymer layer.

7. The sheath of claim 6, wherein a cut or an etch pitch, and a cut or an etch density of the cut, or the etch pattern vary along a length of the reinforcing layer to incorporate various stiffness profiles.

8. The sheath of claim 6, wherein the reinforcing layer comprises a repetitive cut or etch pattern arranged in a plurality of rows, wherein each row comprises a plurality of struts forming a first plurality of enclosed interstices, wherein each of the plurality of enclosed interstices has a central portion, an enclosed first end portion and an enclosed second end portion, wherein the central portion of the interstice has a first width, the first end portion of the interstice has a second width, and the second end portion of the interstice has a third width.

9. The sheath of claim 8, wherein the second width is substantially identical to the third width, or wherein the first width is greater than the second width and the third width, or a combination thereof.

10. The sheath of claim 8, wherein the central portion comprises a first strut and an opposite second strut, and wherein two abut interstices share at least a portion of the first strut or the second strut, wherein each of the first and the second strut has a first end and a second end and a straight portion extending between the first end and the second end;
  wherein each of the first and the second struts split at the first end into a first arm and a second arm in a first slingshot configuration and at the second end into a third arm and a fourth arm in a second slingshot configuration;
  wherein the second arm of the first strut and the first arm of the second strut gather to form an enclosed first end portion; and
  wherein the fourth arm of the first strut and the third arm of the second strut gather to form the enclosed second portion.

11. The sheath of claim 10, wherein at a gathering point, the second arm of the first strut and the first arm of the second strut extend into a first bridging member in a slingshot configuration connecting between the first end portion of the interstice in one row and a second end portion of the interstice in a row below.

12. The sheath of claim 10, wherein at a gathering point the fourth arm of the first strut and the third arm of the second strut extend into a second bridging member connecting the second end portion of the interstice in one row and a first end portion of the interstice in a row above.

13. The sheath of claim 12, wherein two of the first bridging members of each of two abut interstices form a second plurality of enclosed interstices between one row and the row below, and two of the second bridging members of each of two abut interstices form a third plurality of enclosed interstices between one row and the row above.

14. The sheath of claim 10, wherein the straight portion of the first and the second struts have a thickness greater than a thickness of the first, second, third, or fourth arms.

15. The sheath of claim 1, wherein the reinforcing layer comprises a plurality of longitudinally undulating struts, wherein the undulating struts form a plurality of consecutive valleys and apexes, and wherein two longitudinally adjacent struts have an opposite undulation phase such that each of the plurality of valleys of a first strut is proximal to each of the apexes of a first adjacent strut, and wherein each of the apexes of the first strut is proximal to each of the plurality of valleys of a second adjacent strut.

16. The sheath of claim 1, wherein a distal end of the reinforcing layer is different from a proximal end of the reinforcing layer, wherein the distal end of the reinforcing layer comprises an enclosed distal end portion connecting all enclosed interstices present proximally to the enclosed distal end portion, and the enclosed distal end portion comprises a plurality of reflow features configured to integrally connect the distal end of the reinforcing layer with a tip of the sheath,
  wherein the proximal end of the reinforcing layer comprises a plurality of extension struts configured to secure the reinforcing layer to a hub.

17. A method of making a sheath for delivering a medical device comprising:

rolling a reinforcing layer having an inner surface and an outer surface and a first longitudinal edge and an opposite second longitudinal edge, and a width extending from the first edge to the second edge into a spiral configuration around a first mandrel having a first diameter to form a lumen having a rest diameter substantially identical to the first diameter of the mandrel; such that in the spiral configuration, at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration;
  removing the first mandrel;
  inserting a second mandrel having a second diameter larger than the first diameter into the lumen and thereby expanding the lumen to the second diameter by sliding the first edge of the reinforcing layer along at least a portion of the inner surface of the reinforcing layer and sliding the second edge of the reinforcing layer along the at least a portion of the outer surface of the reinforcing layer until the overlapping portion is substantially eliminated and a slit is formed between the first edge and the second edge of the reinforcing layer;
  applying a polymer layer radially outward of the reinforcing layer under conditions effective to encapsulate the reinforcing layer with the polymer layer such that the polymer layer forms a tether portion that is substantially free of the reinforcing layer and wherein the reinforcing layer and the polymer layer together form an inner layer of the sheath;
  removing the inner layer from the second mandrel to allow the reinforcing layer to return to the spiral configuration having a lumen having a diameter substantially identical to the rest diameter; and positioning the inner layer on the first mandrel and applying an outer layer radially outward of the inner layer of the sheath, and removing the sheath from the first mandrel.

18. The method of claim 17, wherein the first edge and/or the second edge of the reinforcing layer comprises a plurality of tabs positioned substantially perpendicular to the first edge and/or the second edge and configured to assist in the step of rolling.

19. A method of delivering a medical device through a sheath, the method comprising:

introducing the medical device into a proximal end of a lumen having a first diameter and wherein the lumen is formed by an inner layer, wherein the inner layer comprises:

a reinforcing layer having an inner surface and an outer surface and a first longitudinal edge and an opposite second longitudinal edge, and wherein the reinforcing layer has a width extending from the first edge to the second edge; and a polymer layer;

wherein the reinforcing layer is rolled longitudinally into a spiral configuration such that at least a portion of the inner surface of the reinforcing layer overlays at least a portion of the outer surface of the reinforcing layer to form an overlapping portion of the spiral configuration, and wherein the first longitudinal edge is slidable along at least a portion of the inner surface of the reinforcing layer and the second longitudinal edge is slidable along at least a portion of the outer surface of the reinforcing layer to increase or decrease the overlapping portion of the spiral configuration, wherein the polymer layer extends circumferentially around the reinforcing layer such that the reinforcing layer is substantially encapsulated within the polymer layer;

wherein the polymer layer comprises a tether portion that is substantially free of the reinforcing layer; and wherein the polymer layer forms a substantially circular enclosed shape of the inner layer;

advancing the medical device through the lumen such that the medical device exerts a radially outward force on the inner layer, such that the lumen expands to a second diameter by sliding the first edge of the reinforcing layer along at least a portion of the inner surface of the reinforcing layer and sliding the second edge of the reinforcing layer along the at least a portion of the outer surface of the reinforcing layer; and locally contracting the expanded sheath back to an unexpanded configuration by radially compressing the expanded portion with a radially inward bias of an outer layer that extends around the inner layer.

20. The method of claim 19, wherein the medical device is a prosthetic heart valve mounted in a radially crimped state on a delivery apparatus, and the act of advancing the medical device through the sheath comprises advancing the delivery apparatus and the prosthetic heart valve into the vasculature of a patient.

* * * * *